(12) United States Patent
Funahashi et al.

(10) Patent No.: US 7,705,183 B2
(45) Date of Patent: Apr. 27, 2010

(54) AROMATIC AMINE DERIVATIVE AND ORGANIC ELECTROLUMINESCENCE DEVICE EMPLOYING THE SAME

(75) Inventors: Masakazu Funahashi, Chiba (JP); Chishio Hosokawa, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 11/550,519

(22) Filed: Oct. 18, 2006

(65) Prior Publication Data

US 2007/0114917 A1    May 24, 2007

(30) Foreign Application Priority Data

Nov. 21, 2005    (JP) .............................. 2005-335434

(51) Int. Cl.
C07C 211/00    (2006.01)
C07F 7/04    (2006.01)

(52) U.S. Cl. ...................... 564/308; 564/307; 564/305; 556/413

(58) Field of Classification Search ........................ None
See application file for complete search history.

(56) References Cited

U.S. PATENT DOCUMENTS

| | | | |
|---|---|---|---|
| 5,187,310 A * | 2/1993 | Mishima et al. | ............ 556/413 |
| 6,307,083 B1 | 10/2001 | Igarashi | |
| 6,310,231 B1 | 10/2001 | Igarashi et al. | |
| 2005/0038296 A1 | 2/2005 | Hosokawa et al. | |
| 2005/0099115 A1 | 5/2005 | Saitoh et al. | |
| 2006/0152146 A1 | 7/2006 | Funahashi | |
| 2006/0189828 A1 | 8/2006 | Hosokawa et al. | |
| 2006/0194074 A1 | 8/2006 | Funahashi | |
| 2006/0210830 A1 | 9/2006 | Funahashi et al. | |
| 2006/0251925 A1 | 11/2006 | Hosokawa et al. | |
| 2008/0207864 A1* | 8/2008 | Nakagawa et al. | ............ 528/25 |

FOREIGN PATENT DOCUMENTS

| | | |
|---|---|---|
| EP | 0 446 895 A1 | 9/1991 |
| EP | 1 491 609 A2 | 12/2004 |
| JP | 3-200889 | 9/1991 |
| JP | 3-271296 | 12/1991 |
| JP | 7-138561 | 5/1995 |
| JP | 8-239655 | 9/1996 |
| JP | 2000-290284 | 10/2000 |
| JP | 2000-351966 | 12/2000 |
| JP | 2001-207167 | 7/2001 |

(Continued)

OTHER PUBLICATIONS

STN; Chemical Abstract Printout 2005:1041220, Abstract of WO2005090365; 2005.*

(Continued)

*Primary Examiner*—Karl J Puttlitz
(74) *Attorney, Agent, or Firm*—Oblon, Spivak, McClelland, Maier & Neustadt, L.L.P.

(57) ABSTRACT

An aromatic amine derivative with a special structure bonding to a fused polycyclic hydrocarbon group having silyl group. An organic electroluminescence device which comprises one or more organic thin film layers comprising at least a light emitting layer sandwiched between a cathode and an anode, wherein at least one of the organic thin film layer comprises the above aromatic amine derivative singly or as its mixture component. An organic electroluminescence device having a long lifetime and an enhanced efficiency of light emission together with the aromatic amine derivatives realizing the device are provided.

10 Claims, 1 Drawing Sheet

FOREIGN PATENT DOCUMENTS

| | | |
|---|---|---|
| JP | 2001-284050 | 10/2001 |
| JP | 2004-204238 | 7/2004 |
| JP | 2005-15420 | 1/2005 |
| JP | 2005-263721 | 9/2005 |
| JP | 2005-268100 | 9/2005 |
| JP | 2005-298485 | 10/2005 |
| JP | 2005-298496 | 10/2005 |
| JP | 2006-62964 | 3/2006 |
| WO | WO 94/06157 | 3/1994 |
| WO | WO 2005/090365 | 9/2005 |
| WO | WO2005090365 A1 * | 9/2005 |

OTHER PUBLICATIONS

Abstract; Breliere et al., Comptes Rendus de l'Academie des Sciences, Serie II: Mecanique, Physique, Chimie, Sciences de la Terre et de l'Univers (1991), 313(13), 1527-32.*

Abstract; Ryabtsova et al., Russian Chemical Bulletin (Translation of Izvestiya Akademii Nauk, Seriya Khimicheskaya) (2001), 50(5), 854-859.*

Abstract; Pozharskii et al., Journal of Organic Chemistry (2003), 68(26).*

Alexander F. Pozharskii, et al., "Organometallic Synthesis, Molecular Structure, and Coloration of 2,7-Disubstituted 1,8-Bis(Dimethylamino)Naphthalenes. How Significant is the Influence of "Buttressing Effect" on Their Basicity?", Journal of Organic Chemistry, vol. 68, No. 26, 2003, pp. 10109-10122.

U.S. Appl. No. 11/736,884, filed Apr. 18, 2007, Hosokawa, et al.

U.S. Appl. No. 11/575,441, filed Mar. 16, 2007, Funahashi.

U.S. Appl. No. 11/596,299, filed Nov. 13, 2006, Funahashi.

C. W. Tang, et al., "Organic electroluminescent diodes", Appl. Phys. Lett., vol. 51, No. 12. Sep. 21, 1987, pp. 913-915.

* cited by examiner

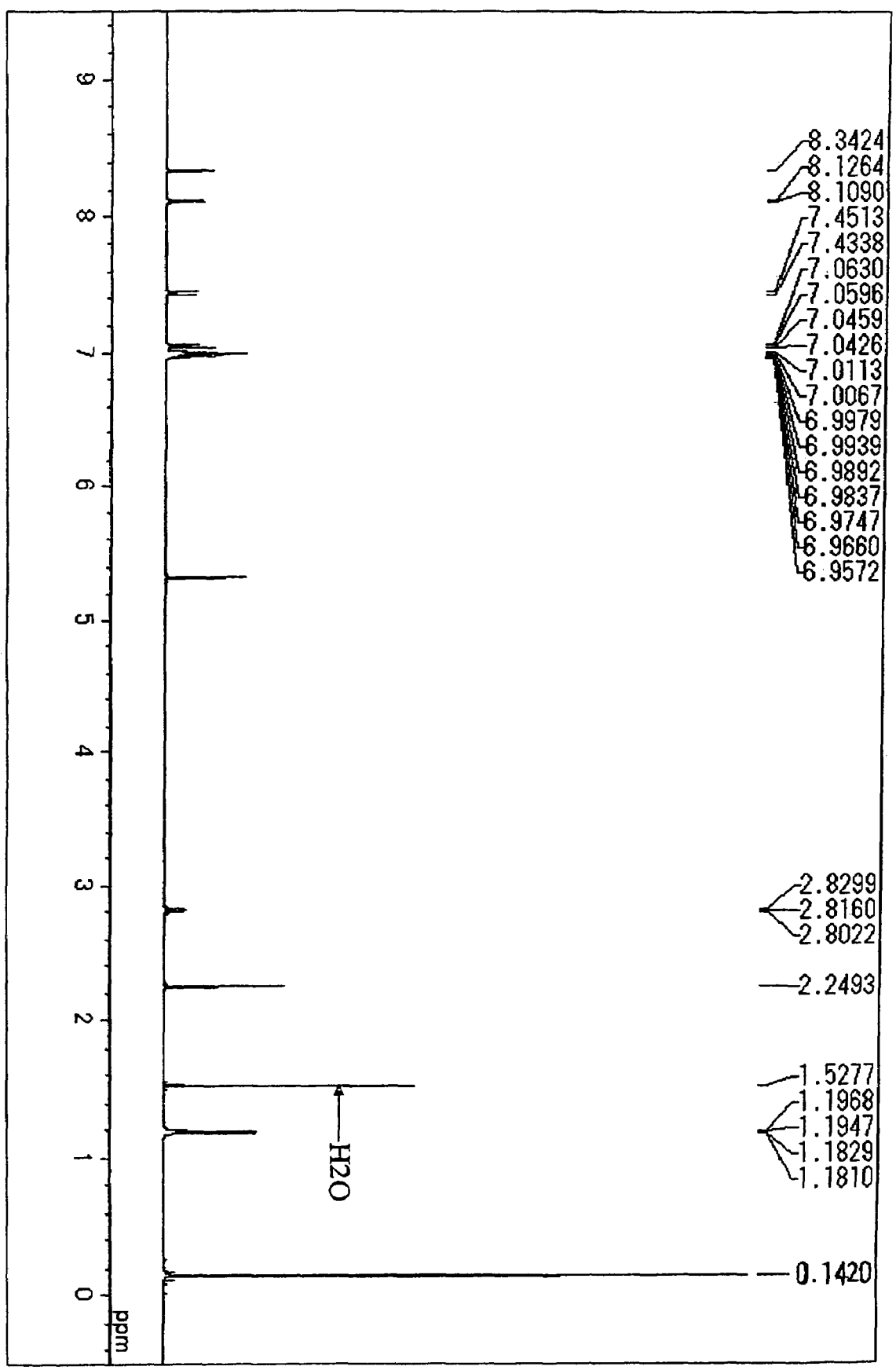

AROMATIC AMINE DERIVATIVE AND ORGANIC ELECTROLUMINESCENCE DEVICE EMPLOYING THE SAME

TECHNICAL FIELD

The present invention relates to an aromatic amine derivative and an organic electroluminescence ("electroluminescence" will be occasionally referred to as "EL", hereinafter) device employing the derivative. More particularly, it relates to an organic EL device having a prolonged lifetime and an enhanced efficiently of light emission, together with an aromatic amine derivative realizing the organic EL device.

BACKGROUND ART

An organic electroluminescence device is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported by C. W. Tang et al. of Eastman Kodak Company (C. W. Tang and S. A. Vanslyke, Applied Physics Letters, Volume 51, Page 913, 1987), many studies have been conducted on organic EL devices using organic materials as the constituting materials.

Tang et al. used a laminate structure using tris(8-quinolinolato)aluminum for the light emitting layer and a triphenyldiamine derivative for the hole transporting layer. Advantages of the laminate structure are that the efficiency of hole injection into the light emitting layer can be increased, that the efficiency of forming excited particles which are formed by blocking and recombining electrons injected from the cathode can be increased, and that excited particles formed among the light emitting layer can be enclosed. As the structure of the organic EL device, a two-layered structure having a hole transporting (injecting) layer and an electron transporting and light emitting layer and a three-layered structure having a hole transporting (injecting) layer, a light emitting layer and an electron transporting (injecting) layer are well known. To increase the efficiency of recombination of injected holes and electrons in the devices of the laminate type, the structure of the device and the process for forming the device have been studied.

As the light emitting material of the organic EL device, chelate complexes such as tris(8-quinolinolato)aluminum, coumarin complexes, tetraphenylbutadiene derivatives, bis-styrylarylene derivatives and oxadiazole derivatives are known. It is reported that light in the visible region ranging from blue light to red light can be obtained by using these light emitting materials, and development of a device exhibiting color images is expected (For example, refer to Patent Literatures 1 to 3 below). However, they were not sufficient because their efficiency of light emission and lifetime did not achieve at a practical level yet.

Further, an organic EL device which emits blue light with a long lifetime employing a distyryl compound adding styrylamine or so as an organic blue-light emitting material is proposed (refer to Patent Literature 4 below). However, the device described therein fails to show a sufficiently long lifetime and, therefore, further improvement has been demanded. Furthermore, a technique of employing mono or bis anthracene compound and a distyryl compound as an organic light emitting medium layer is disclosed (refer to Patent Literature 5 below). However in these technology, a conjugated structure of the styryl compound lengthened wavelength of a light emission spectrum and deteriorated the purity of color Still further, Patent Literature 6 below discloses an organic EL device employing aminoanthracene derivative as an organic green-light emitting material. Despite the disclosure, the above material has a low glass transition temperature and the organic EL device employing the above material reveals poor heat resistance and failed in achieving long lifetime and enhanced efficiency of light emission.

Patent Literature 1: Japanese Unexamined Patent Application Laid-Open No. Heisei 8(1996)-239655
Patent Literature 2: Japanese Unexamined Patent Application Laid-Open No. Heisei 7(1995)-138561
Patent Literature 3: Japanese Unexamined Patent Application Laid-Open No. Heisei 3(1991)-200289
Patent Literature 4: International Application Published under PCT No. WO 94/006157
Patent Literature 5: Japanese Unexamined Patent Application Laid-Open No. 2001-284050
Patent Literature 6: Japanese Unexamined Patent Application Laid-Open No. 2001-207167

DISCLOSURE OF THE INVENTION

The present invention has been made to overcome the above problems. An object of the present invention is to provide organic EL devices having a long lifetime and an enhanced efficiency of light emission, and to provide aromatic amine derivatives capable of realizing such organic EL devices.

As a result of extensive researches for developing aromatic amine derivatives having the above suitable properties and organic EL devices using the aromatic amine derivatives, the inventors have found that the object of the present invention can be achieved by using aromatic amine derivatives represented by a following general formula (I) whose central skeleton is a fused polycyclic hydrocarbon group having a silyl group. The present invention has been accomplished on the basis of the above finding.

Thus, the present invention provides an aromatic amine derivative represented by the following general formula (I):

In the general formula (I), X represents a substituted or unsubstituted fused polycyclic hydrocarbon group having 10 to 50 ring carbon atoms.

$A_1$ to $A_4$ each independently represents a substituted or unsubstituted aryl group having 5 to 50 ring carbon atoms, a substituted or unsubstituted alkyl group having 1 to 50 carbon atoms, a substituted or unsubstituted cycloalkyl group having 3 to 50 ring carbon atoms, a substituted or unsubstituted aralkyl group having 6 to 50 ring carbon atoms or a substituted or unsubstituted heterocyclic group having 5 to 50 ring carbon atoms.

R₁ represents a substituted or unsubstituted silyl group having 3 to 20 carbon atoms.

R₂ represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxyl group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted heterocyclic group having 5 to 50 ring carbon atoms.

a represents an integer of 0 to 3, b represents an integer of 1 to 4, c represents an integer of 0 to 4, and when a, b or c is 2 or greater, the content of the parenthesis, i.e., ( ) may be the same with or different from each other.

The present invention provides an organic EL device which comprises one or more organic thin film layers comprising at least a light emitting layer sandwiched between a cathode and an anode, wherein at least one of the organic thin film layer comprises the aromatic amine derivative singly or as its mixture component.

The organic EL device employing the aromatic amine derivative of the present invention reveals practically sufficient luminance even under low applied voltage, exhibits an enhanced efficiency of light emission, and is not apt to degrade even after a long time usage demonstrating a prolonged lifetime.

BRIEF DESCRIPTION OF THE DRAWING

FIG. 1 is a chart showing ¹H-Nuclear Magnetic Resonance (NMR) spectrum of the Compound (D-3-2) of the present invention obtained in Synthesis Example 1 (3).

PREFERRED EMBODIMENT TO CARRY OUT THE INVENTION

The present invention provides an aromatic amine derivative represented by a following general formula (I):

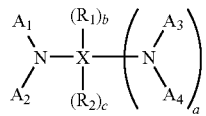

In the general formula (I), X represents a substituted or unsubstituted fused polycyclic hydrocarbon group having 10 to 50 (preferably 10 to 30) ring carbon atoms.

$A_1$ to $A_4$ each independently represents a substituted or unsubstituted aryl group having 5 to 50 (preferably 5 to 20) ring carbon atoms, a substituted or unsubstituted alkyl group having 1 to 50 (preferably 1 to 20) carbon atoms, a substituted or unsubstituted cycloalkyl group having 3 to 50 (preferably 3 to 12) ring carbon atoms, a substituted or unsubstituted aralkyl group having 6 to 50 (preferably 6 to 20) ring carbon atoms or a substituted or unsubstituted heterocyclic group having 5 to 50 (preferably 5 to 20) ring carbon atoms.

$R_1$ represents a substituted or unsubstituted silyl group having 3 to 20 (preferably 3 to 12) carbon atoms.

$R_2$ represents a hydrogen atom, a substituted or unsubstituted alkyl group having 1 to 50 (preferably 1 to 20) carbon atoms, a substituted or unsubstituted aryl group having 5 to 50 (preferably 5 to 20) ring carbon atoms, a substituted or unsubstituted aralkyl group having 6 to 50 (preferably 6 to 20) ring carbon atoms, a substituted or unsubstituted cycloalkyl group having 3 to 50 (preferably 5 to 12) ring carbon atoms, a substituted or unsubstituted alkoxyl group having 1 to 50 (preferably 1 to 6) carbon atoms, a substituted or unsubstituted aryloxy group having 5 to 50 (preferably 5 to 18) ring carbon atoms, a substituted or unsubstituted arylamino group having 5 to 50 (preferably 5 to 18) ring carbon atoms, a substituted or unsubstituted alkylamino group having 1 to 20 (preferably 1 to 6) carbon atoms, a substituted or unsubstituted heterocyclic group having 5 to 50 (preferably 5 to 20) ring carbon atoms.

Examples of the substituted or unsubstituted fused polycyclic hydrocarbon group represented by X include a moiety of naphthalene, phenanthrene, fluoranthene, anthracene, pyrene, perylene, coronene, chrysene, picene, diphenylanthracene, fluorene, triphenylene, rubicene, benzanthracene, phenylanthracene, bisanthracene, dianthracenylbenzene or dibenzanthracene, etc.

Examples of the substituted or unsubstituted alkyl group represented by $A_1$ to $A_4$ or $R_2$ include methyl group, ethyl group, propyl group, isopropyl group, butyl group, sec-butyl group, tert-butyl group, pentyl group, hexyl group, heptyl group, octyl group, stearyl group, trichloromethyl group, trifluoromethyl group, etc.

Examples of the substituted or unsubstituted aryl group represented by $A_1$ to $A_4$ or $R_2$ include phenyl group, 2-methylphenyl group, 3-methylphenyl group, 4-methylphenyl group, 4-ethylphenyl group, biphenyl group, 4-methylbiphenyl group, 4-ethylbiphenyl group, 4-cyclohexylbiphenyl group, terphenyl group, 3,5-dichlorophenyl group, naphthyl group, 5-methylnaphthyl group, anthryl group, pyrenyl group, etc.

Examples of the cycloalkyl group represented by $A_1$ to $A_4$ or $R_2$ include cyclopropyl group, cyclobutyl group, cyclopentyl group, cyclohexyl group, etc.

Examples of the substituted or unsubstituted aralkyl group represented by $A_1$ to $A_4$ or $R_2$ include benzyl group, α,α-methylphenylbenzyl group, triphenylmethyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, α-phenoxybenzyl group, α-benzyloxybenzyl group, α,α-ditrifluoromethylbenzyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group, etc.

Examples of the substituted or unsubstituted heterocyclic group represented by $A_1$ to $A_4$ or $R_2$ include pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morpholidinyl group, piperazinyl group, triatynyl group, carbazolyl group, furanyl group, thiophenyl group, oxazolyl group, oxadiazolyl group, benzoxazolyl group, thiazolyl group, thiadiazolyl group, benzothiazolyl group, triazolyl group, imidazolyl group, benzimidazolyl group, pranyl group, etc.

Examples of the substituted or unsubstituted silyl group represented by $R_1$ include trimethylsilyl group, triethylsilyl group, t-butyldimethylsilyl group, vinyldimethylsilyl group, propyldimethylsilyl group, triphenylsilyl group, etc.

Examples of the substituted or unsubstituted alkoxyl group represented by $R_2$ include methoxy group, ethoxy group, propoxy group, isopropoxy group, butoxy group, isobutoxy group, sec-butoxy group, tert-butoxy group, various kinds of pentyloxy groups, various kinds of hexyloxy groups, etc.

Examples of the substituted or unsubstituted aryloxy group represented by $R_2$ include phenoxy group, tolyloxy group, naphthyloxy group, etc.

Examples of the substituted or unsubstituted arylamino group represented by $R_2$ include diphenylamino group, ditolylamino group, dinaphthylamino group, naphthylphenylamino group, etc.

Examples of the substituted or unsubstituted alkylamino group represented by $R_2$ include dimethylamino group, diethylamino group, dihexylamino group, etc.

In the general formula (I), a represents an integer of 0 to 3 (preferably 0 to 2), b represents an integer of 1 to 4 (preferably 1 to 2), c represents an integer of 0 to 4 (preferably 0 to 2), and when a, b and/or c is 2 or greater, the content of the parenthesis, i.e., ( ) may be the same with or different from each other.

It is preferable that the aromatic amine derivative represented by the general formula (I) of the present invention has a structure represented by a following general formula (II):

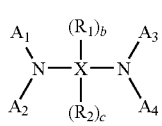

(II)

In the general formula (II), X, $A_1$ to $A_4$, $R_1$, $R_2$, b and c are the same as the above description about the foregoing general formula (I) respectively.

Further, it is preferable that the aromatic amine derivative represented by the general formula (I) of the present invention has a structure represented by a following general formula (III):

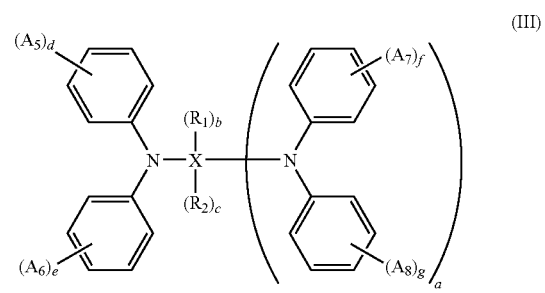

(III)

In the general formula (III), X, $R_1$, $R_2$, a, b and c are the same as the above description about the foregoing general formula (I) respectively.

$A_5$ to $A_8$ each independently represents a hydrogen atom, a substituted or unsubstituted alkyl group having 1 to 50 (preferably 1 to 20) carbon atoms, a substituted or unsubstituted aryl group having 5 to 50 (preferably 5 to 20) ring carbon atoms, a substituted or unsubstituted aralkyl group having 6 to 50 (preferably 6 to 20) ring carbon atoms, a substituted or unsubstituted cycloalkyl group having 3 to 50 (preferably 5 to 12) ring carbon atoms, a substituted or unsubstituted alkoxyl group having 1 to 50 (preferably 1 to 6) carbon atoms, a substituted or unsubstituted aryloxy group having 5 to 50 (preferably 5 to 18) ring carbon atoms, a substituted or unsubstituted arylamino group having 5 to 50 (preferably 5 to 18) ring carbon atoms, a substituted or unsubstituted alkylamino group having 1 to 20 (preferably 1 to 6) carbon atoms, a substituted or unsubstituted silyl group having 3 to 20 (preferably 3 to 12) carbon atoms or a substituted or unsubstituted heterocyclic group having 5 to 50 (preferably 5 to 20) ring carbon atoms Examples of the substituted or unsubstituted alkyl group, the substituted or unsubstituted aryl group, the substituted or unsubstituted aralkyl group, the substituted or unsubstituted cycloalkyl group, the substituted or unsubstituted alkoxyl group, the substituted or unsubstituted aryloxy group, the substituted or unsubstituted arylamino group, the substituted or unsubstituted alkylamino group, the substituted or unsubstituted silyl group and the substituted or unsubstituted heterocyclic group each represented by $A_5$ to $A_8$ in the general formula (III) include the same examples as about the $A_1$ to $A_4$, $R_1$ and $R_2$ in the general formula (I) or the general formula (II).

In the general formula (III), d, e, f and g each independently represents an integer of 0 to 5 (preferably 0 to 3), and when d, e, f and/or g is an integer of 2 or greater, plural of $A_5$ to $A_8$ may be the same with or different from each other, and may bond each other to form a saturated or unsaturated ring.

Examples of the ring include cycloalkane having 4 to 12 carbon atoms such as cyclobutane, cyclopentane, cyclohexane, adamantane, norbornane, etc.; cycloalkene having 4 to 12 carbon atoms such as cyclobutene, cyclopentene, cyclohexene, cycloheptene, cyclooctene, etc.; cycloalkadiene having 6 to 12 carbon atoms such as cyclohexadiene, cycloheptadiene, cyclooctadiene, etc.; and aromatic ring having 6 to 50 carbon atoms such as benzene, naphthalene, phenanthrene, anthracene, pyrene, chrysene, acenaphthylene, etc.

Specific examples of the aromatic amine derivatives represented by the general formula (I) will be shown below, though not particularly limited thereto.

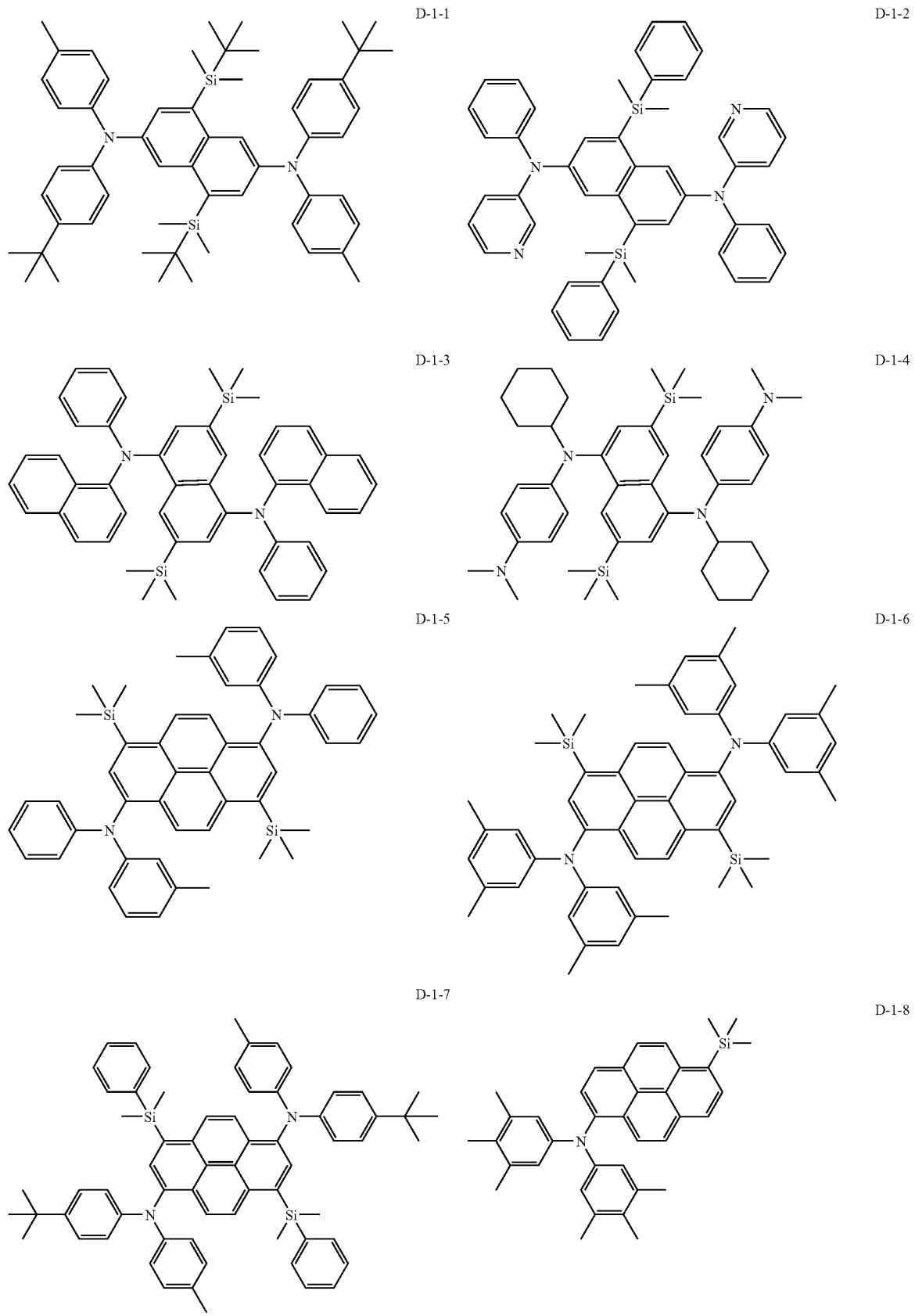

-continued
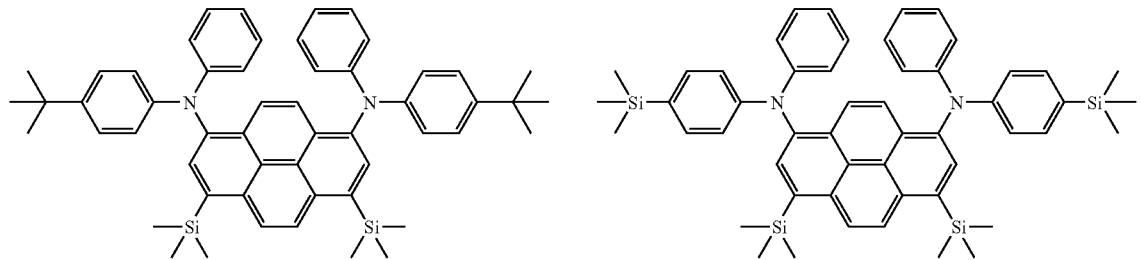
D-1-9  D-1-10
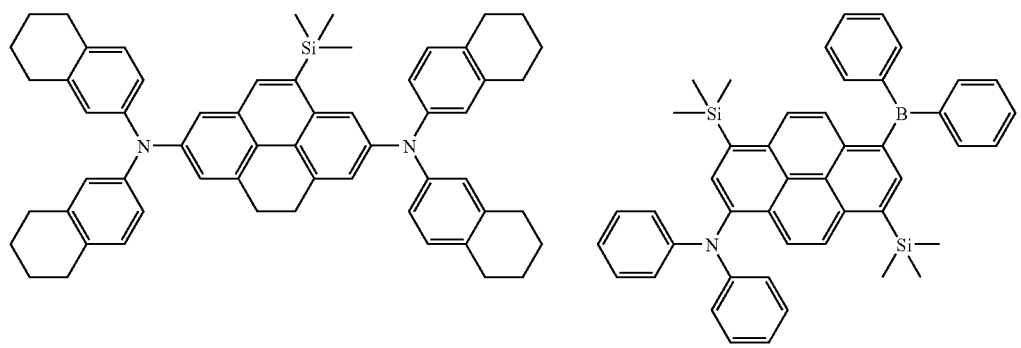
D-1-11  D-1-12
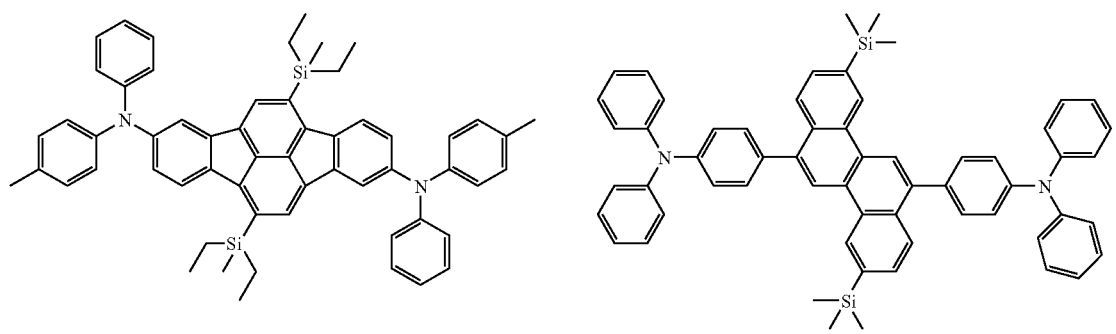
D-2-1  D-2-2
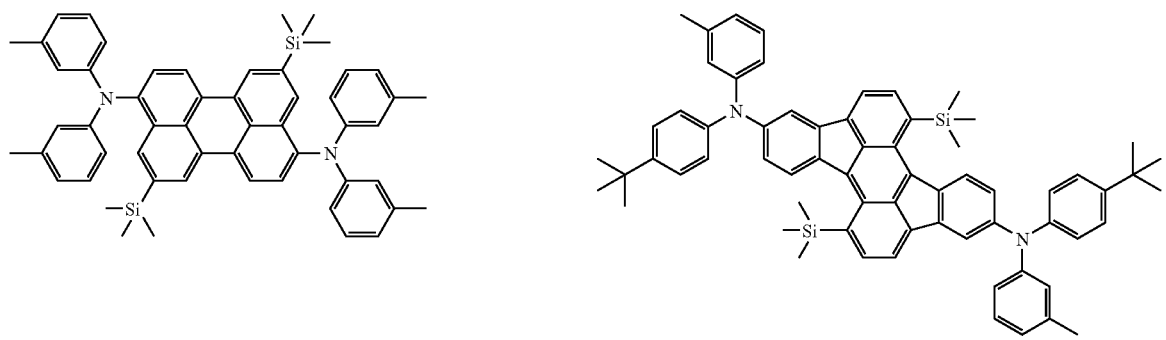
D-2-3  D-2-4

-continued
D-2-5
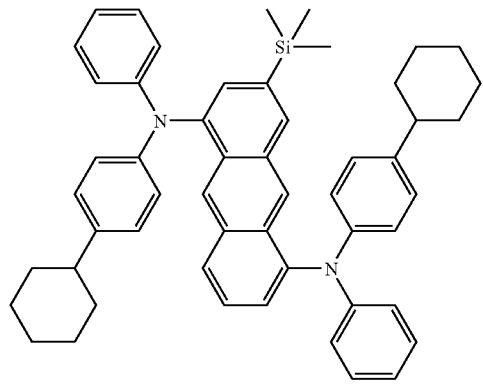
D-2-6
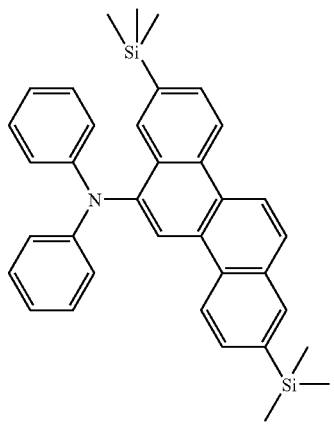
D-2-7
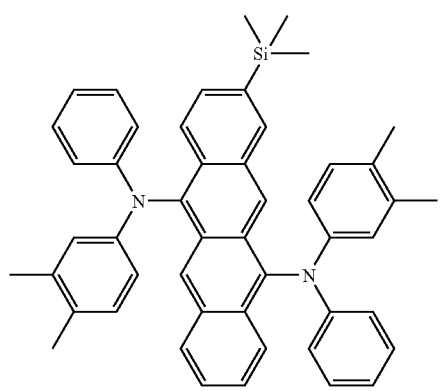
D-2-8
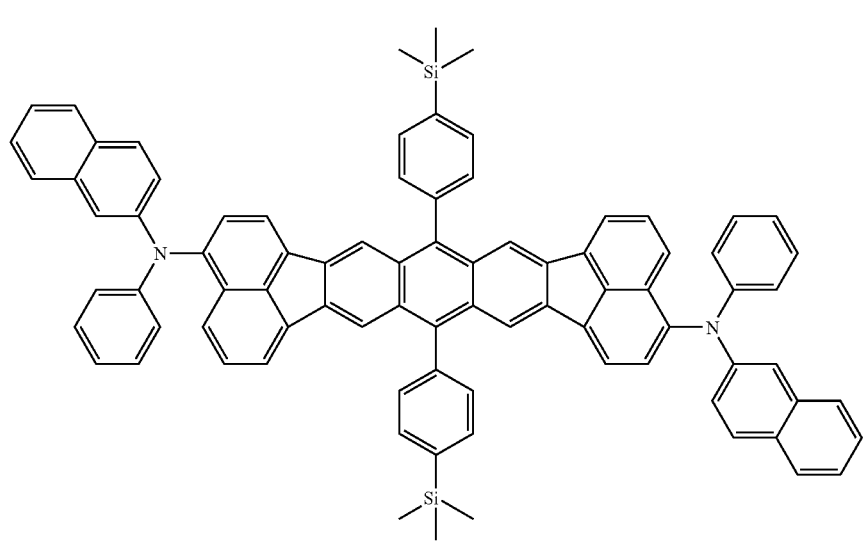

-continued
D-2-9
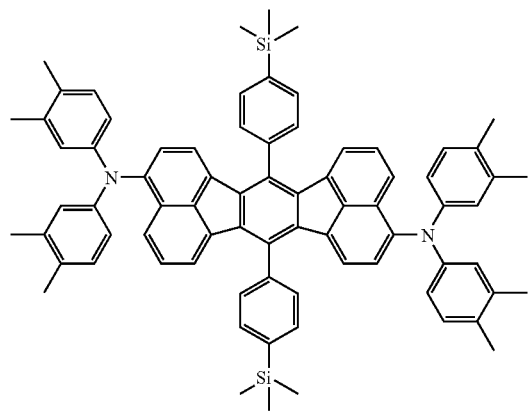
D-3-1
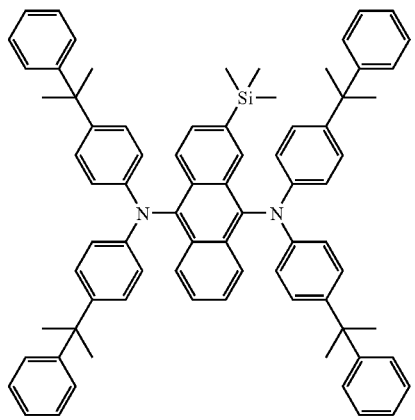
D-3-2
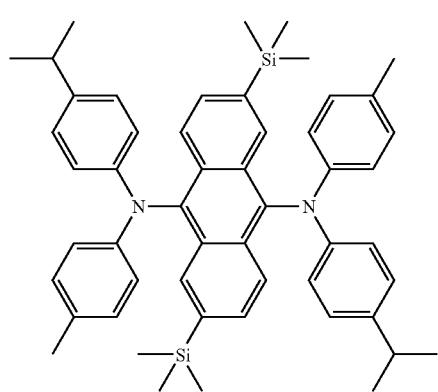
D-3-3
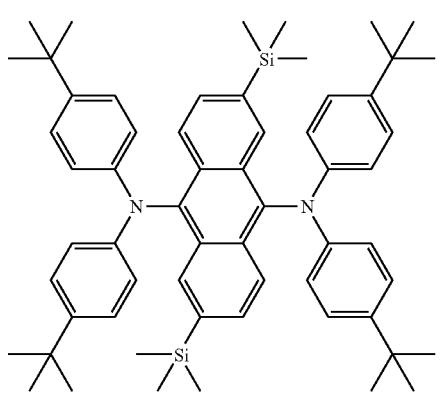
D-3-4
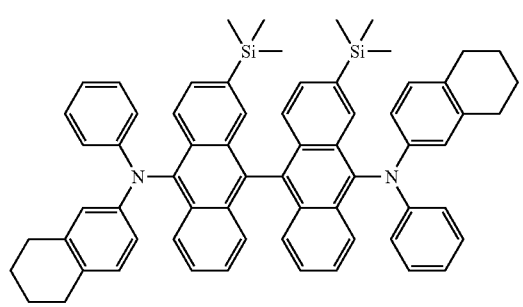
D-3-5
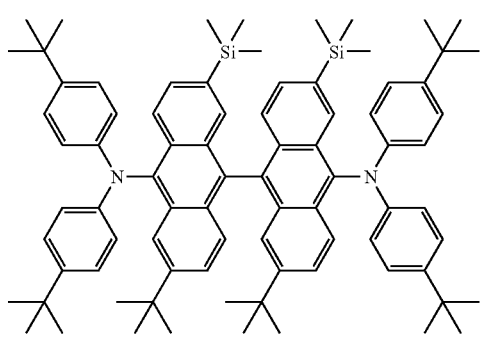
D-3-6
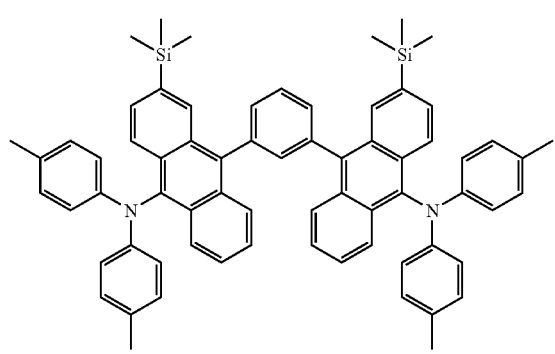
D-3-7
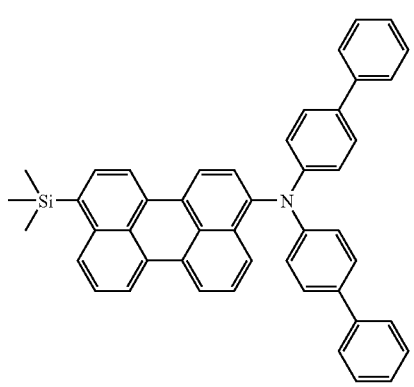

-continued

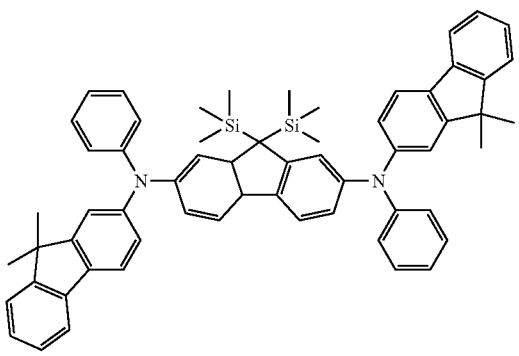

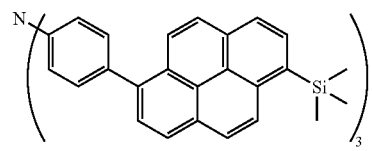

D-3-9

In the aromatic amine derivative represented by any one of the general formulae (I), (II) and (III) of the present invention, since the silyl group is owned by the fused polycyclic hydrocarbon structure as a light emission center, the association between the compounds is prevented, resulting in a prolonged lifetime thereof. Moreover, because bonding a bulky substituent to the fused polycyclic hydrocarbon skeleton increases a steric repulsion against the amine structure, the lifetime prolongs further.

Furthermore, the aromatic amine derivative of the present invention has powerful fluorescent property in solid state, is superior in an electric field electroluminescent property and has a fluorescent quantum efficiency of 0.3 or more. Still further, because it has a superior hole injection property or a superior hole transportation property from a metal electrode or from an organic thin layer, and a superior electron injection property or a superior electron transportation property from the metal electrode or from the organic thin layer, it is effectively employed as an light emitting material, particularly as a doping material, for an organic EL device. Moreover, still other hole injecting and transporting material, electron injecting and transporting material or a doping material may be employed.

The organic EL device of the present invention is a device comprising one or more organic thin film layers sandwiched between an anode and a cathode. When the organic thin film is a single layer type, a light emitting layer is sandwiched between the anode and the cathode. The light emitting layer contains the light emitting material and may further contain a hole injecting material and an electron injecting material in order to effectively transport holes injected from the anode or electrons injected from the cathode to the light emitting material. The aromatic amine derivative of the present invention has an enhanced light emitting property and excellent hole injecting ability and hole transporting ability as well as excellent electron injecting ability and electron transporting ability and, therefore, can be used as a light emitting material or a doping material in the light emitting layer.

In the organic EL device of the present invention, the light emitting layer contains the aromatic amine derivative of the present invention singly or as a mixture component. The content is usually 0.1 to 20% by weight and more preferably 1 to 10% by weight. Further, the aromatic amine derivatives of the present invention exhibit not only an extremely high fluorescent quantum efficiency but also high hole transporting ability and electron transporting ability, and further are capable of forming a uniform thin film, so that the light emitting layer may be formed from the aromatic amine derivatives only.

On the other hand, in the case where the organic EL device of the present invention comprises two or more organic thin film layers having at least the light emitting layer which are sandwiched between the cathode and the anode, the organic thin film layers preferably include an organic layer containing the aromatic amine derivative of the present invention as an essential component which is disposed between the anode and the light emitting layer. Such an organic layer may be a hole injecting layer, a hole transporting layer, etc.

Further, in a case where the aromatic amine derivative of the present invention is employed as a doping material, it is preferable that at least one kind selected from the group consisting of anthracene derivatives of a following general formula (3), anthracene derivatives of a following general formula (4) and pyrene derivatives of a following general formula (5) is employed as a host material.

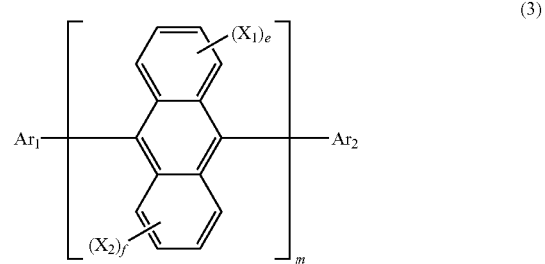

(3)

In the general formula (3), $X_1$ and $X_2$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxyl group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted heterocyclic group having 5 to 50 ring carbon atoms or a halogen atom; e and f each independently represents an integer of 0 to 4; when e or f is 2 or greater, plural of $X_1$ or $X_2$ may be the same with or different from each other.

$Ar_1$ and $Ar_2$ each independently represents a substituted or unsubstituted aryl group having 5 to 50 ring carbon atoms or a substituted or unsubstituted heterocyclic group having 5 to 50 ring carbon atoms; at least one of $Ar_1$ or $Ar_2$ represents a substituted or unsubstituted aryl group with a fused ring and having 10 to 50 ring carbon atoms.

m represents an integer of 1 to 3; when m is 2 or greater, a group within a parentheses: [ ] may be the same with or different from each other. Specific examples and substituents of the $X_1$, $X_2$, $Ar_1$ and $Ar_2$ are the same as those explained about the foregoing general formula (I).

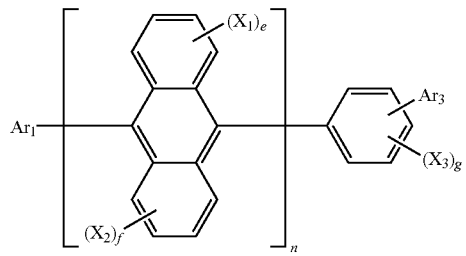
(4)

In the general formula (4), $X_1$ to $X_3$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxyl group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted heterocyclic group having 5 to 50 ring carbon atoms or a halogen atom; e, f, and g each independently represents an integer of 0 to 4; when e, f, or g is 2 or greater, plural of $X_1$, $X_2$ or $X_3$ may be the same with or different from each other.

$Ar_1$ represents a substituted or unsubstituted aryl group with a fused ring and having 10 to 50 ring carbon atoms; $Ar_3$ represents a substituted or unsubstituted aryl group having 5 to 50 ring carbon atoms.

n represents an integer of 1 to 3; when n is 2 or greater, a group within a parentheses: [ ] may be the same with or different from each other.

Specific examples and substituents of the $X_1$ to $X_3$, $Ar_1$ and $Ar_3$ are the same as those explained about the foregoing general formula (I).

Specific examples of anthracene derivative represented by the general formulae (3) and (4) will be shown below, though not particularly limited thereto.

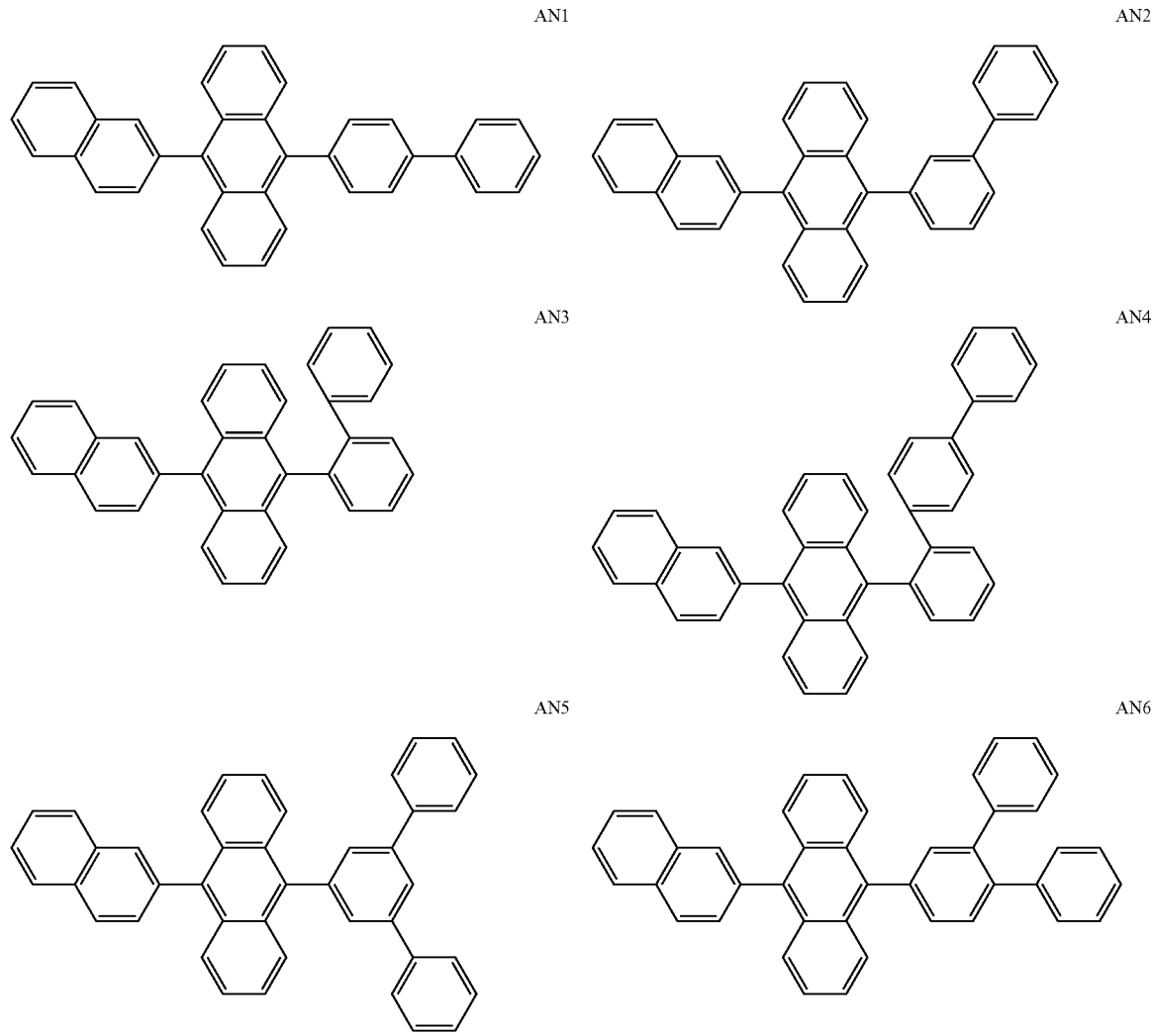

-continued
AN7
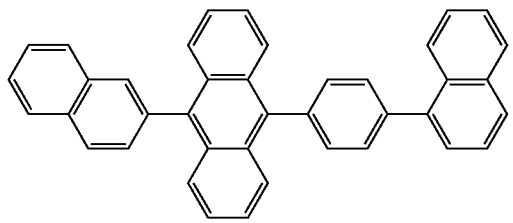
AN8
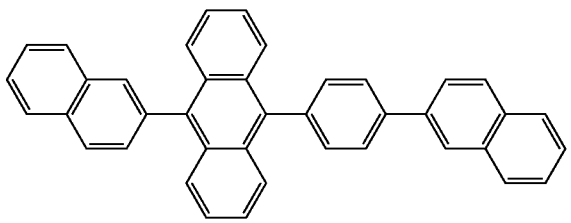
AN9
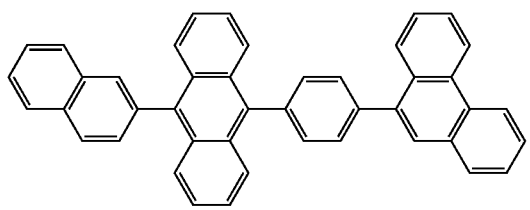
AN10
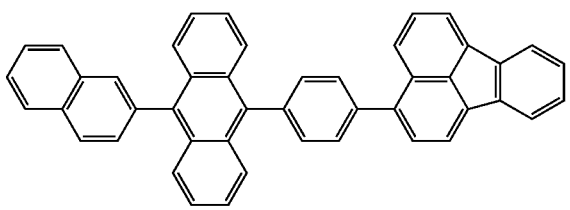
AN11
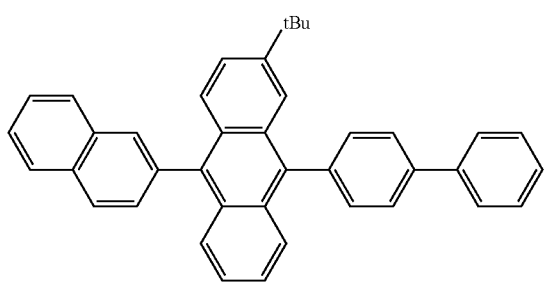
AN12
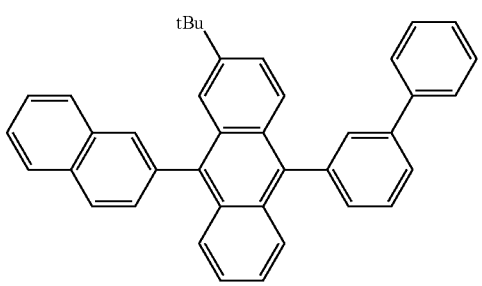
AN13
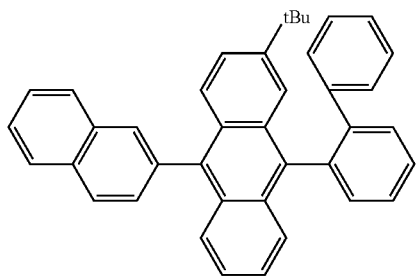
AN14
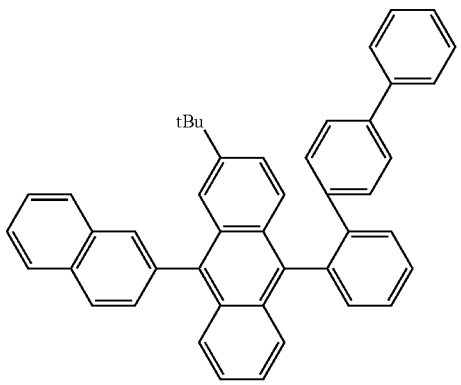
AN15
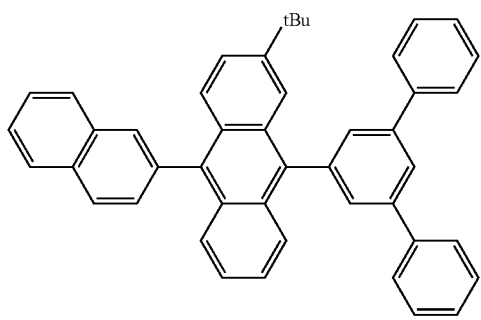
AN16
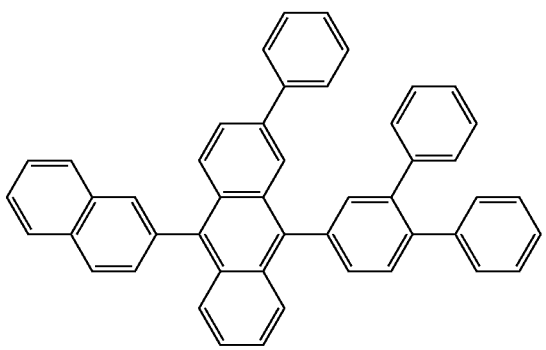

-continued
AN17
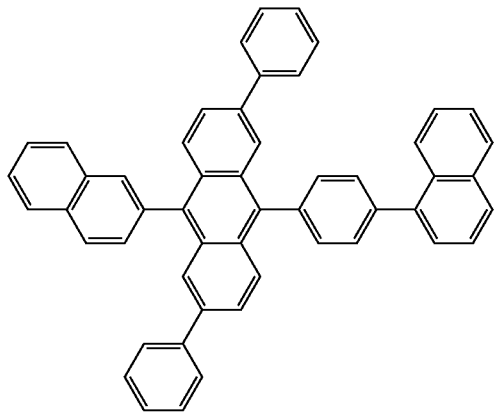
AN18
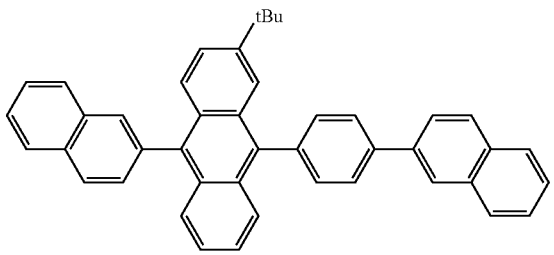
AN19
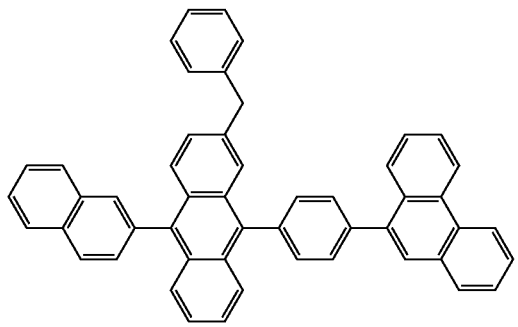
AN20
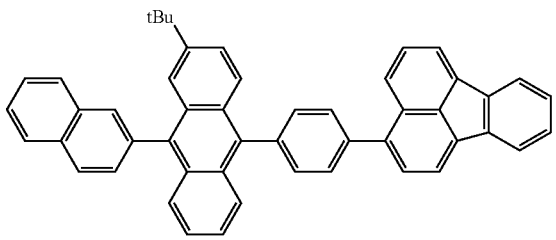
AN21
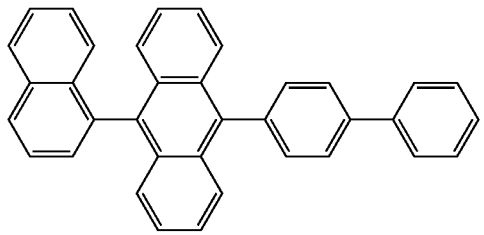
AN22
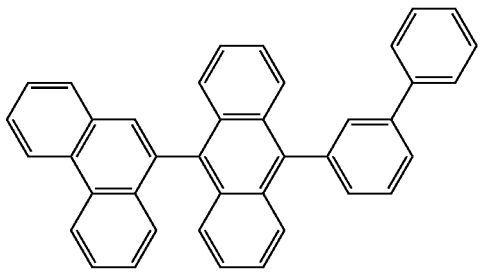
AN23
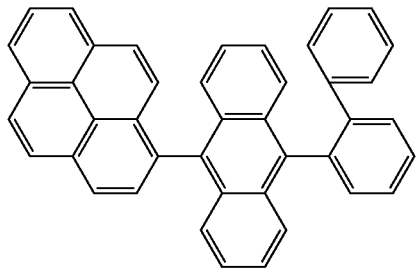
AN24
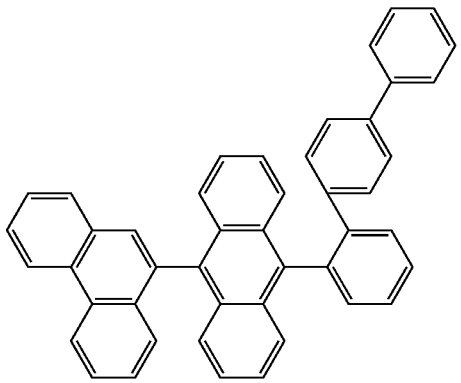

-continued
AN25
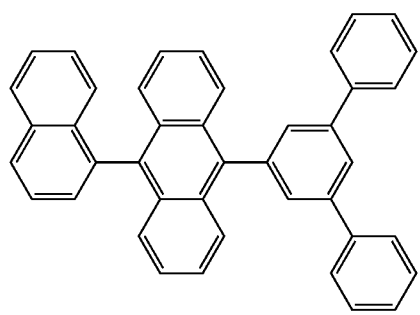
AN26
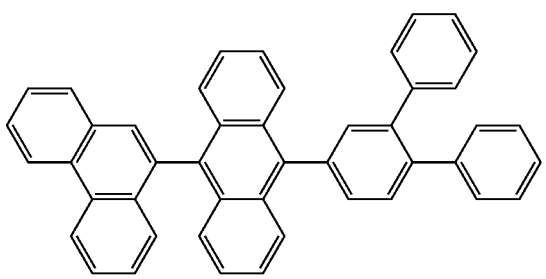
AN27
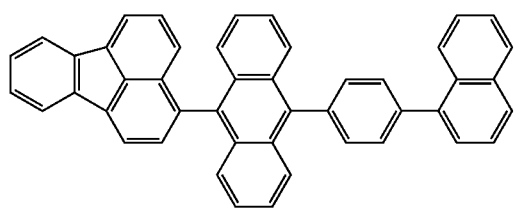
AN28
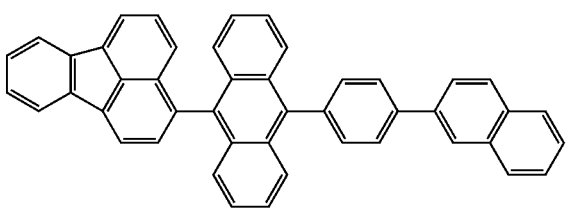
AN29
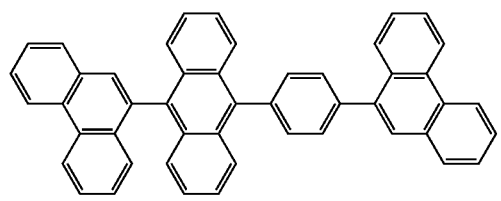
AN30
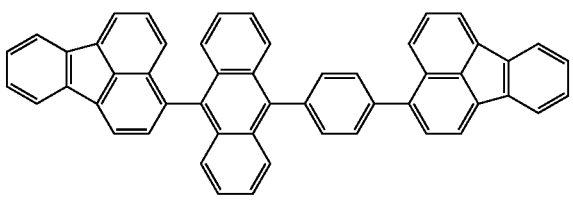
AN31
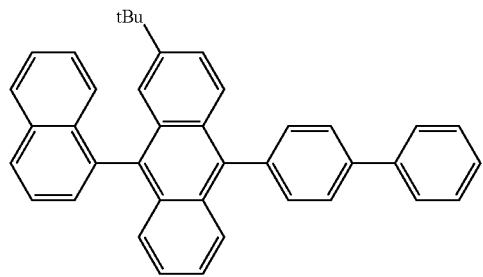
AN32
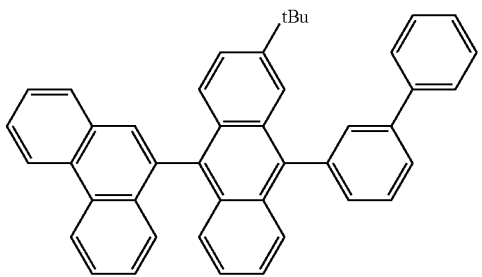
AN33
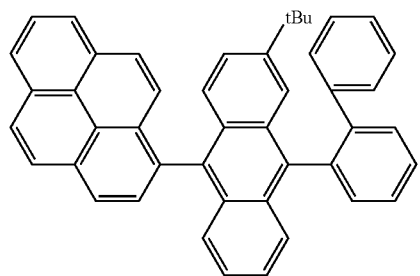
AN34
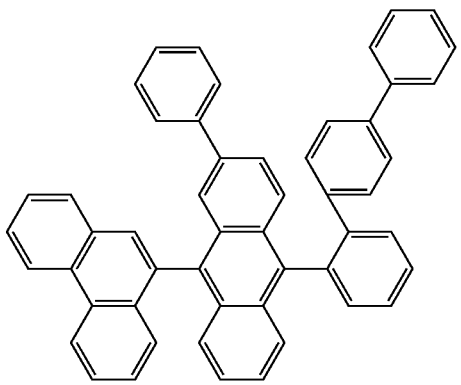

-continued
AN35
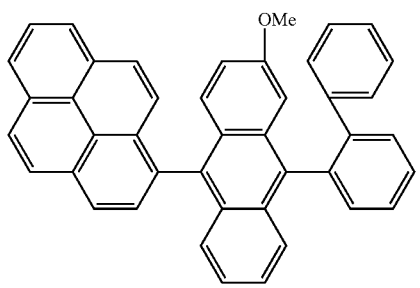
AN36
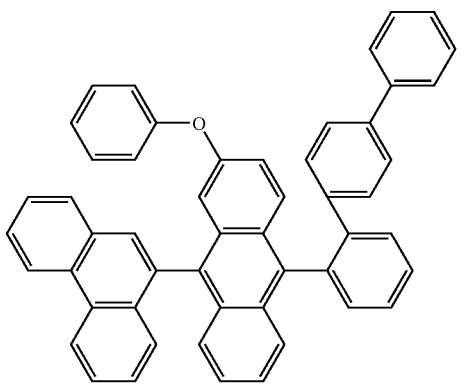
AN37
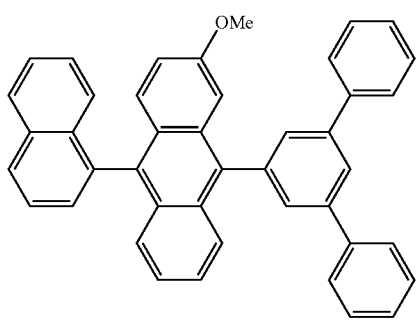
AN38
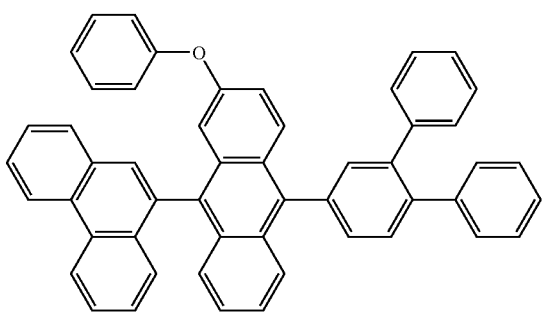
AN39
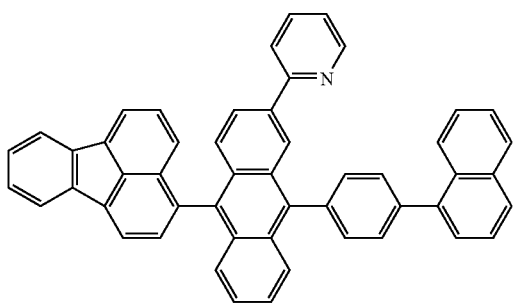
AN40
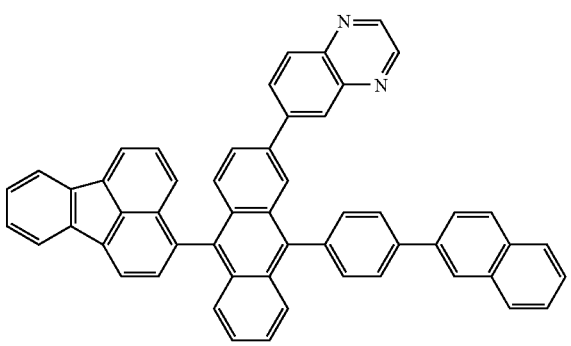
AN41
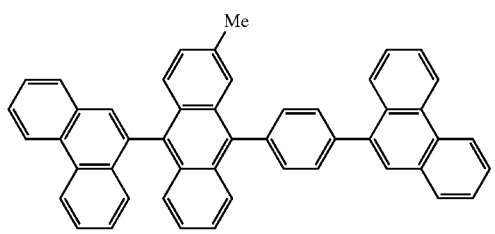
AN42
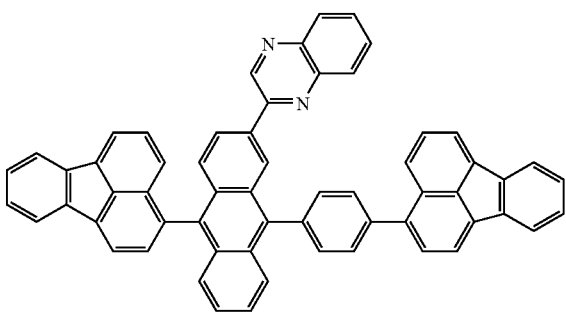

-continued

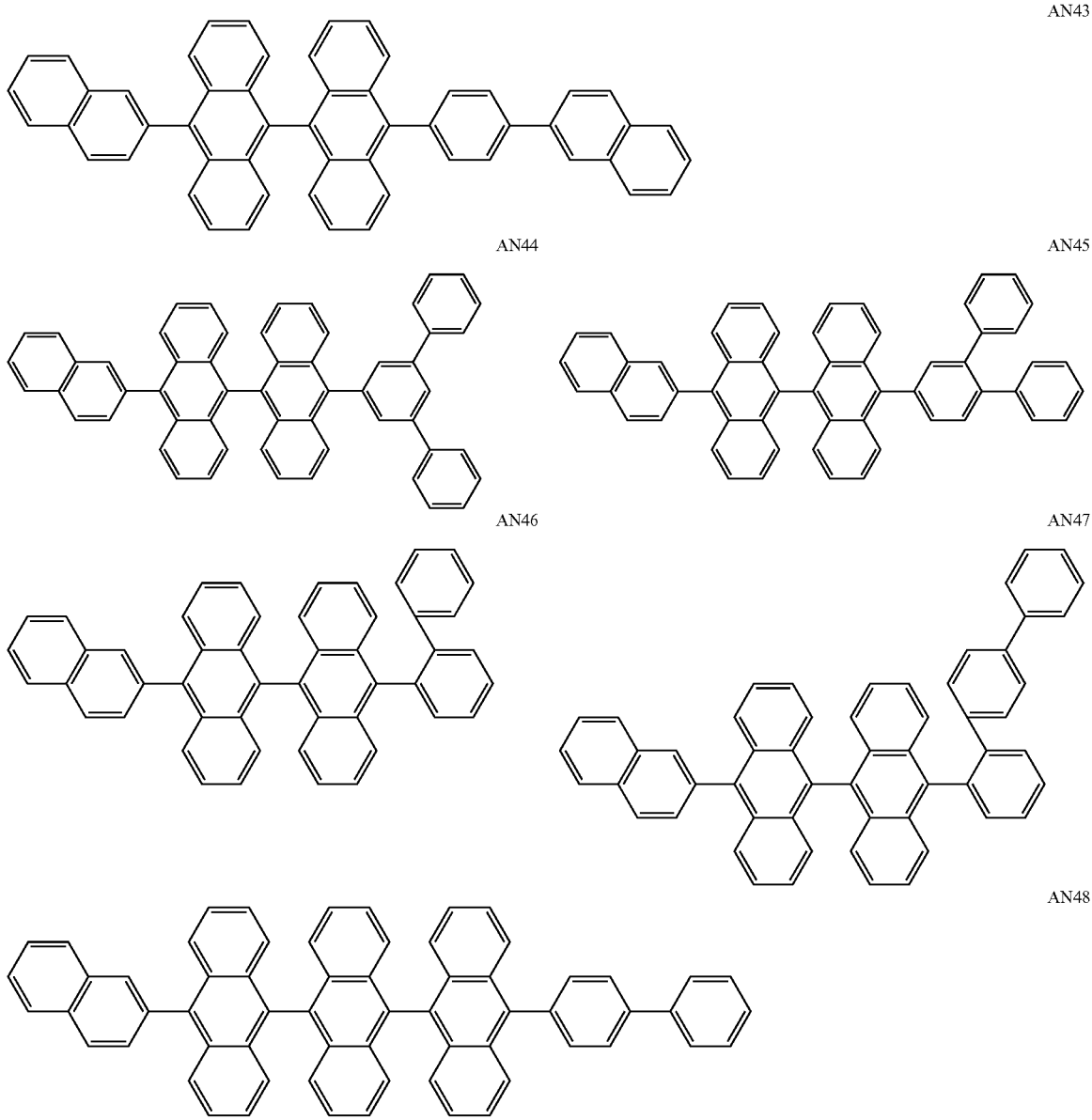

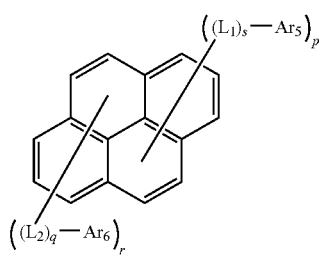

In the general formula (5), $Ar_5$ and $Ar_6$ each independently represents a substituted or unsubstituted aryl group having 6 to 50 ring carbon atoms.

$L_1$ and $L_2$ each independently represents a substituted or unsubstituted phenylene group, a substituted or unsubstituted naphthalenylene group, a substituted or unsubstituted fluorenylene group or a substituted or unsubstituted dibenzosilolylene group.

s represents an integer of 0 to 2, p represents an integer of 1 to 4, q represents an integer of 0 to 2 and r represents an integer of 0 to 4.

Further, $L_1$ or $Ar_5$ bonds to any one of 1 to 5 position of pyrene, also $L_2$ or $Ar_6$ bonds to any one of 6 to 10 position thereof.

However, when p+r is an even number, $Ar_5$, $Ar_6$, $L_1$ and $L_2$ satisfy a following requirement (1) or a requirement (2):

(1) $Ar_5 \neq Ar_6$ and/or $L_1 \neq L_2$ (wherein ≠ means that each group has a different structure)

(2) When $Ar_5 = Ar_6$ and $L_1 = L_2$ (2-1) s≠q and/or p≠r, or (2-2) When s=q and p=r, (2-2-1) Both $L_1$ and $L_2$ or pyrene each bonds respectively to different positions of $Ar_5$ and $Ar_6$, or (2-2-2) Both $L_1$ and $L_2$ or pyrene each bonds respectively to the same position of $Ar_5$ and $Ar_6$, excluding a case where a pyrene derivative having both $L_1$ and $L_2$ or both $Ar_5$ and $Ar_6$ bond to 1 and 6 positions thereof, or 2 and 7 positions thereof.

Specific examples and substituents of the $Ar_5$, $Ar_6$, $L_1$ and $L_2$ are the same as those explained about the foregoing general formula (I)

Specific examples of the pyrene derivative represented by the general formula (5) will be shown below, though not particularly limited thereto.

P1

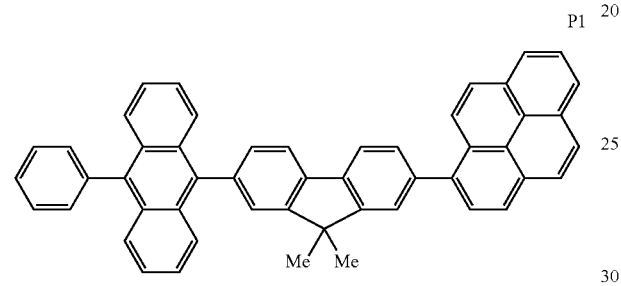

P2

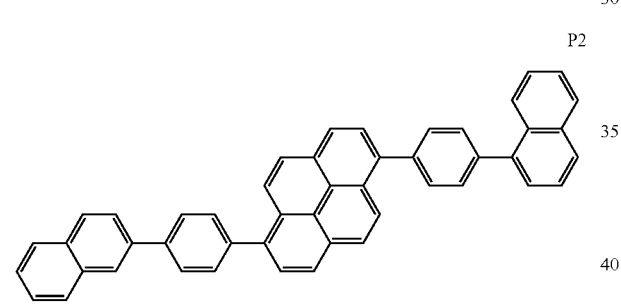

P3

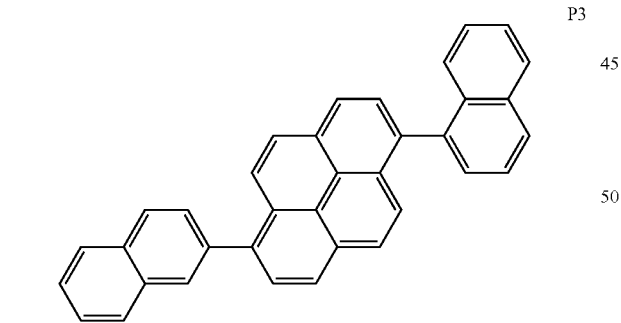

P4

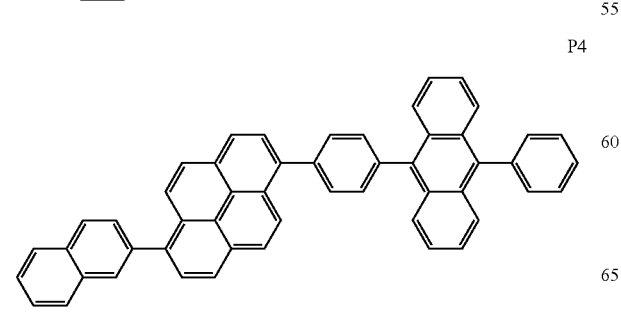

-continued

P5

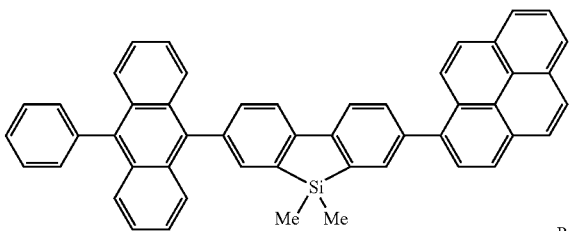

P6

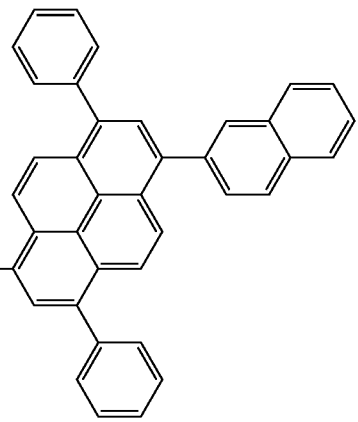

P7

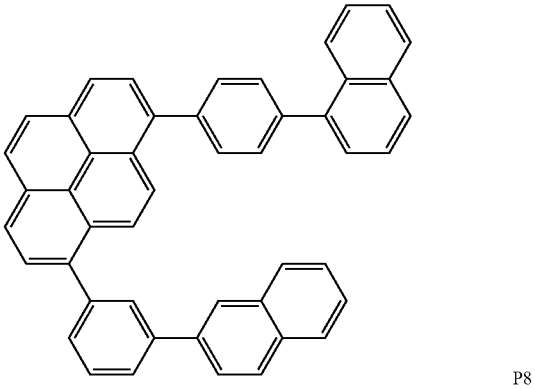

P8

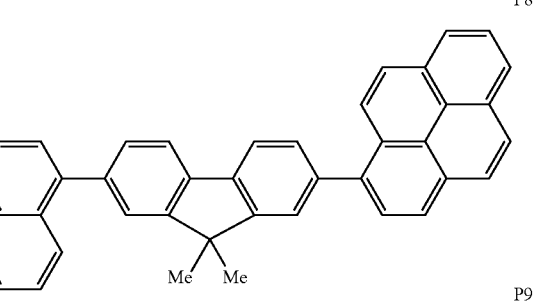

P9

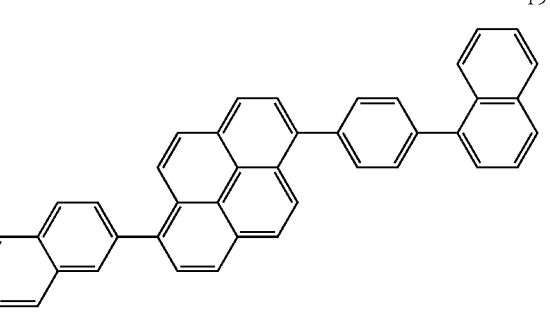

-continued
P10
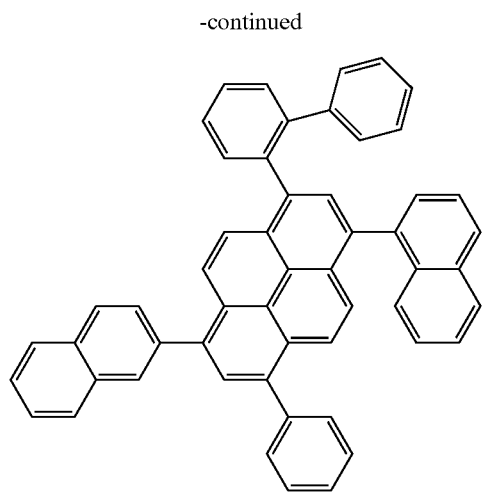
P11
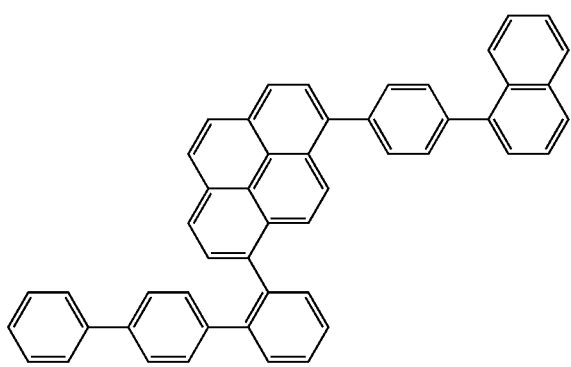
P12
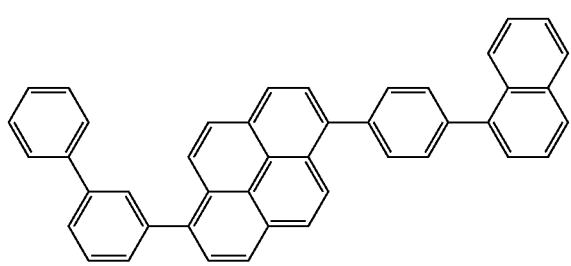
P13
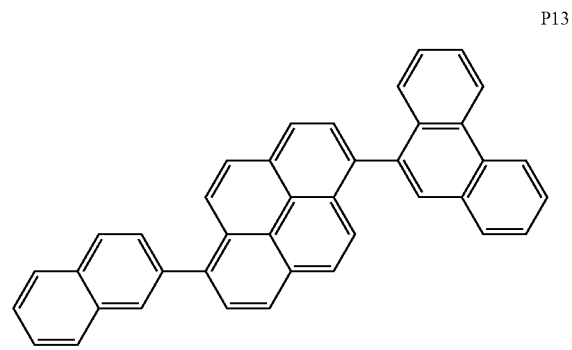
-continued
P14
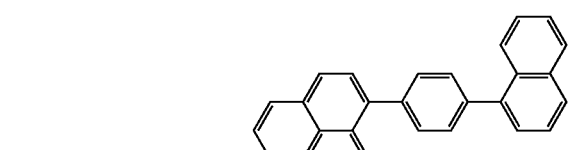
P15
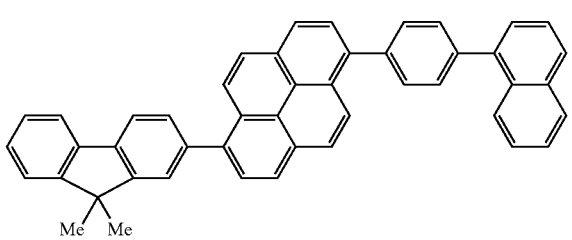
P16
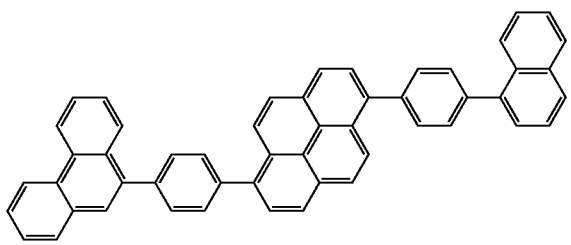
P17
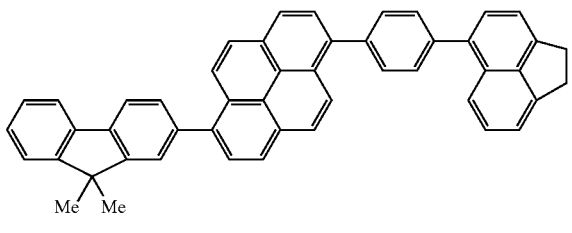
P18
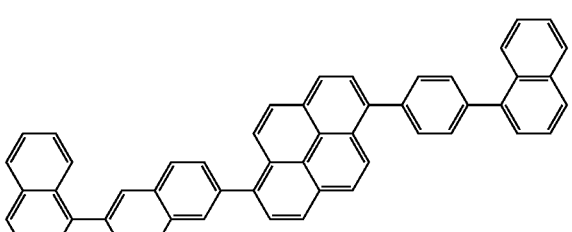

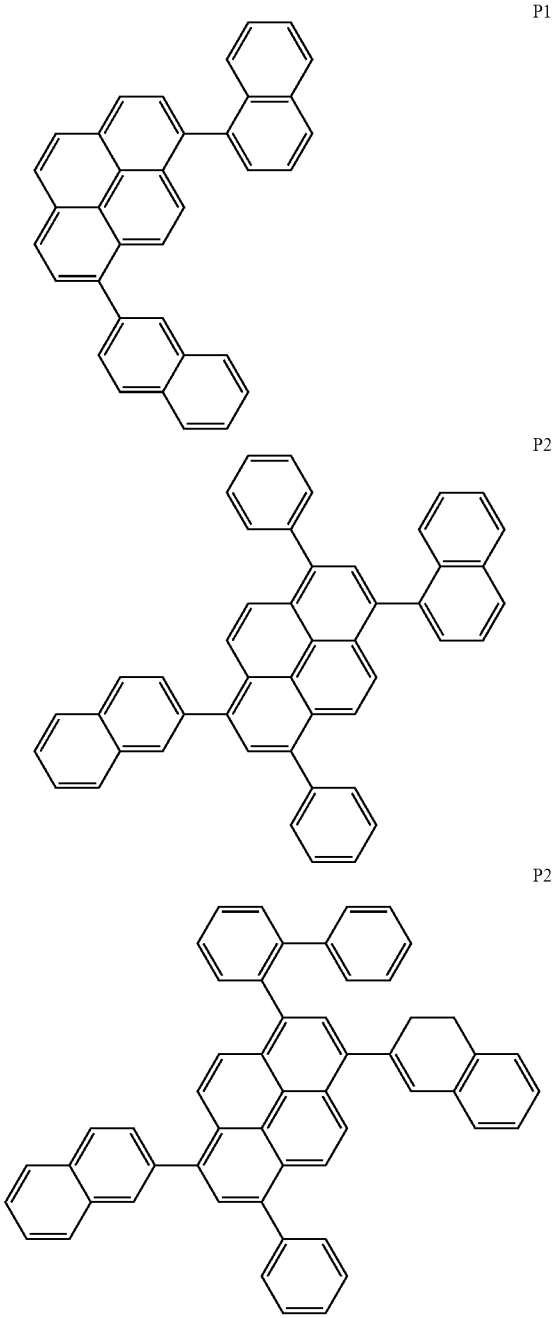

In the present invention, examples of the organic EL device of a multilayer type include those having multilayer structures such as (an anode/a hole injecting layer/a light emitting layer/a cathode), (an anode/a light emitting layer/an electron injecting layer/a cathode) and (an anode/a hole injecting layer/a light emitting layer/an electron injecting layer/a cathode).

The multilayer may also optionally contain, in addition to the aromatic amine derivatives of the present invention, conventionally known materials such as light emitting materials, doping materials, hole injecting materials and electron injecting materials according to requirements. The organic EL device having such a multilayer structure can be prevented from suffering from deterioration in luminance and lifetime due to quenching. If required, the light emitting materials, doping materials, hole injecting materials and electron injecting materials may be used in combination with each other. The use of the doping materials enables the resultant device to be improved in luminance of light emitted and efficiency of light emission, and further emit a red color light or a blue color light. Further, in the organic EL device of the present invention, the hole injecting layer, the light emitting layer and the electron injecting layer may respectively have a multilayer structure including two or more layers. In this case, the multi-layer hole injecting layer may include a hole injecting layer into which holes are injected from the electrode, and a hole transporting layer for accepting the holes from the hole injecting layer and transporting the holes to the light emitting layer. Also, the multi-layer electron injecting layer may include an electron injecting layer into which electrons are injected from the electrode, and an electron transporting layer for accepting the electrons from the electron injecting layer and transporting the electrons to the light emitting layer. These respective layers may be selectively used according to various factors such as energy level of the materials used, heat resistance, and adhesion to the organic thin film layers or the metal electrodes.

Examples of the host material or the doping material besides the foregoing general formulae (3) to (5) employable for the light emitting layer together with the aromatic amine derivative of the present invention include fused polycyclic aromatic compound such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenyl-ethynyl)anthracene, 1,4-bis(9'-ethynylanthracenyl)benzene and those derivatives; organometallic complex such as tris(8-quinolinolato)aluminum, bis-(2-methyl-8-quinolinolato)-4-(phenylphenolinato) aluminum, etc.; triarylamine derivative, styrylamine derivative, stilbene derivative, coumarin derivative, pyran derivative, oxazone derivative, benzothiazole derivative, benzoxazole derivative, benzimidazole derivative, pyrazine derivative, cinnamate ester derivative, diketopyrrolopyrrole derivative, acridone derivative, quinacridone derivative, etc.; though not particularly limited thereto.

The hole injecting material is preferably made of compounds which have a hole transporting ability as well as excellent capabilities of accepting holes injected from the anode and injecting the holes into the light emitting layer or light emitting material, prevent excited particles produced in the light emitting layer from moving into the electron injecting layer or electron injecting material, and exhibit an excellent capability of forming a thin film. Specific examples of the hole injecting material include phthalocyanine derivatives, naphthalocyanine derivatives, porphyrin derivatives, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkanes, stilbene, butadiene, benzidine-type triphenylamine, styryl amine-type triphenylamine, diamine-type triphenylamine and derivatives thereof, as well as polyvinylcarbazoles, polysilanes, and polymer materials such as electroconductive polymers, though not particularly limited thereto.

Of those hole injecting materials employable in the organic EL device of the present invention, more effective hole injecting materials are aromatic tertiary amine derivatives and phthalocyanine derivatives.

Specific examples of the aromatic tertiary amine derivatives include triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cylcohexane, and oligomers and polymers having these aromatic tertiary amine skeletons, though not particularly limited thereto.

Specific examples of the phthalocyanine (Pc) derivatives include phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, GaPc-O—GaPc, as well as naphthalocyanine derivatives though not particularly limited thereto. Also, in the organic EL device of the present invention, between the light emitting layer and the anode, there is preferably provided a layer containing these aromatic tertiary amine derivatives and/or phthalocyanine derivatives, such as the above hole transporting layer or hole injecting layer.

The electron injecting material is preferably made of compounds which have a good electron transporting ability as well as excellent capabilities of accepting electrons injected from the cathode and injecting the electrons into the light emitting layer or light emitting material, prevent excited particles produced in the light emitting layer from moving into the hole injecting layer, and exhibit an excellent capability of forming a thin film. Specific examples of the electron injecting material include fluorenone, anthraquinodimethane, diphenoquinone, thiopyrane dioxide, oxazole, oxadiazole, triazole, imidazole, perylenetetracarboxylic acid, fluorenylidenemethane, anthraquinodimethane, anthrone, and derivatives thereof, though not particularly limited thereto. Further, an electron accepting substance and an electron donating substance may be added to the hole injecting material and the electron injecting material, respectively, for enhanced sensitization thereof.

In the organic EL device of the present invention, among those electron injecting materials, more effective electron injecting materials are metal complex compounds and five-member ring derivatives having a nitrogen atom.

Specific examples of the metal complex compounds include 8-hydroxyquinolinatolithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, and bis(2-methyl-8-quinolinato)(2-naphtholato)gallium, though not particularly limited thereto.

The five-member ring derivatives having a nitrogen atom are preferably derivatives of oxazole, thiazole, oxadiazole, thiadiazole or triazole. Specific examples include 2,5-bis(1-phenyl)-1,3,4-oxazole, dimethyl POPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole, and 1,4-bis[2-(5-phenyltriazolyl)]benzene, though not particularly limited thereto.

In the organic EL device of the present invention, the light emitting layer may also optionally contain, in addition to the aromatic amine derivatives represented by the general formula (I) at least one material selected from the group consisting of light emitting materials, doping materials, hole injecting materials and electron injecting materials. The organic EL device of the present invention may be further provided on a surface thereof with a protective layer, or the entire part thereof may be protected with silicone oil, resins, etc., in order to enhance stability thereof against temperature, humidity, atmosphere, etc.

The anode of the organic EL device according to the present invention may be suitably made of an electroconductive material having a work function exceeding 4 eV. Examples of the electroconductive material for the anode include carbon, aluminum, vanadium, iron, cobalt, nickel, tungsten, silver, gold, platinum, palladium and alloys thereof, metal oxides such as tin oxide and indium oxide which are used for ITO substrates or NESA substrates, and organic electroconductive resins such as polythiophene and polypyrrole. The cathode of the organic EL device according to the present invention may be suitably made of an electroconductive material having a work function of less than 4 eV. Examples of the electroconductive material for the cathode include magnesium, calcium, tin, lead, titanium, yttrium, lithium, ruthenium, manganese, aluminum, lithium fluoride and alloys thereof, though not particularly limited thereto. Typical examples of the alloys include alloys of magnesium and silver, alloys of magnesium and indium, and alloys of lithium and aluminum, though not particularly limited thereto. The ratio between the constituting metals in the alloys may be controlled and appropriately determined depending upon temperature of vapor deposition sources, atmosphere, vacuum degree, etc. The anode and cathode may be constituted of two or more layers, if required.

At least one surface of the organic EL device of the present invention preferably exhibits a sufficient transparency in a wavelength range of light emitted therefrom in order to enhance an efficiency of light emission thereof. Further, the substrate for the device is also preferably transparent. The transparent electrode is formed using the above electroconductive material by vapor deposition process, sputtering process, etc., so as to ensure a desirable transparency thereof. The electrode disposed on a light emitting surface of the device preferably has a light transmittance of 10% or greater. The substrate is not particularly limited as long as it suitably has a good mechanical and thermal strength as well as a good transparency. Examples of the substrate include glass substrates and transparent resin films. Specific examples of the transparent resin films include films made of polyethylene, ethylene-vinyl acetate copolymer, ethylene-vinyl alcohol copolymer, polypropylene, polystyrene, polymethylmethacrylate, polyvinyl chloride, polyvinyl alcohol, polyvinylbutyral, nylons, polyether ether ketones, polysulfones, polyethersulfones, tetrafluoroethylene-perfluoroalkylvinylether copolymer, polyvinyl fluoride, tetrafluoroethylene-ethylene copolymer, tetrafluoroethylene-hexafluoropropylene copolymer, polychlorotrifluoroethylene, polyvinylidenefluoride, polyesters, polycarbonates, polyurethanes, polyimide, polyether imides, polypropylene, etc.

The respective layers of the organic EL device of the present invention may be formed by either a dry film-forming process such as vacuum vapor deposition process, sputtering process, plasma process and ion-plating process, or a wet film-forming process such as spin-coating process, dipping process and flow-coating process. The thickness of the respective layers is not particularly limited, but should be adjusted to an appropriate range. When the thickness is too thick, a great electric voltage must be applied to the device in order to achieve a predetermined light output, resulting in a poor efficiency of light emission. On the other hand, when the thickness is too thin, pinholes tend to be formed in the layers, thereby failing to obtain a sufficient luminance of light emission even upon applying an electric field thereto. The suitable thickness of the respective layers is usually in the range of from 5 nanometers to 10 μm and preferably from 10 nanometers to 0.2 μm.

In the wet film-forming process, materials constituting the respective layers are dissolved or dispersed in a suitable solvent such as ethanol, chloroform, tetrahydrofuran and dioxane to form a thin film thereof. The solvent used for forming the respective layers is not particularly limited. Also, suitable resins or additives may be added to the respective organic thin film layers for the purposes of improving a film-forming property, preventing formation of pinholes in the resultant film, etc. Examples of the resins usable for the above purposes include insulating resins such as polystyrene, polycarbonates, polyarylates, polyesters, polyamides, polyurethanes, polysulfones, polymethylmethacrylate, polymethylacrylate and celluloses as well as copolymers thereof, photoconductive resins such as poly-N-vinylcarbazole and polysilanes, and electroconductive resins such as polythiophene and polypyrrole. Examples of the additives include antioxidants, ultraviolet absorbers and plasticizers, etc.

The organic EL device of the present invention is suitably applied to, for example, planar light-emitting members such as a flat panel displays or so for wall-hanging type televisions, copiers, printers, back light for liquid crystal displays and light sources for measuring equipments, display panels, marker light, etc. Further, the material of the present invention can be used not only for organic EL devices but also in other applications such as electrophotographic members, photoelectric converters, solar cells, image sensors, etc.

EXAMPLE

The present invention shall be explained below in further details with reference to examples.

Synthesis Example 1

Synthesis of Compound (D-3-2)

(1) Synthesis of 2,6-bis(trimethylsilyl)anthracene

Under an atmospheric argon gas flow, 2,6-dibromoanthracene in an amount of 2.8 g (8.3 millimole), dried tetrahydrofuran (THF) in an amount of 200 milliliter and dried toluene in an amount of 200 milliliter were placed into a three necked-flask equipped with a cooling pipe and having a capacity of 1 liter and then, the resultant solution was cooled down to −30° C. Subsequently, n-butyllithium in an amount of 12 milliliter (19.1 millimole, 1.58 M hexane solution) was added slowly. Then, after adding trimethylsilylchloride in an amount of 2.4 milliliter (19.1 millimole, d=0.85) at a temperature of −70° C., the resultant solution was stirred at a room temperature for 1 hour. After completing the reaction, 100 milliliter of water was added and an organic layer was separated. The solution was dried with a use of sodium sulfate and then, the solvent was separated by distillation, and the residue was washed with a use of 100 milliliter of methanol and as a result, 1.7 g of pale yellow powder was obtained (the yield: 57%).

(2) Synthesis of 9,10-dibromo-2,6-bis(trimethylsilyl)anthracene

Under an atmospheric argon gas flow, 2,6-bis(trimethylsilyl)anthracene in an amount of 1.7 g (5.6 millimole), N-bromosuccinimide in an amount of 2.5 g (11.3 millimole) and dried dimethylformamide (DMF) in an amount of 300 milliliter were placed into an eggplant flask equipped with a cooling pipe and having a capacity of 1 liter, and the resultant solution was stirred at a room temperature for 5 hours. After completing the reaction, 300 milliliter of water was added and precipitated crystal was separated by filtration, washed with uses of water in an amount of 50 milliliter and methanol in an amount of 100 milliliter and then, purifying it by means of column chromatography (silicagel, developing solvent: hexane), 1.2 g of pale yellow powder was obtained (the yield: 46%).

(3) Synthesis of Compound (D-3-2)

Under an atmospheric argon gas flow, 9,10-dibromo-2,6-bis(trimethylsilyl)anthracene in an amount of 1.2 g (2.5 millimole), 4-methyl-4'-isopropyl diphenylamine in an amount of 1.4 g (6.2 millimole), palladium acetate in an amount of 0.01 g (1.5% by mole), tri-t-butylphosphine in an amount of 0.02 g (3% by mole), sodium t-butoxide in an amount of 0.6 g (6.2 millimole) and dried toluene in an amount of 50 milliliter were placed into a three-neck flask equipped with a cooling pipe and having a capacity of 300 milliliter, and the resultant solution was stirred with heating at a temperature of 100° C. for one night. After completing the reaction, precipitated crystal was separated by filtration and washed with the use of 50 milliliter of toluene and 100 milliliter of methanol, and as a result, 1.7 g of pale yellow powder was obtained. The pale yellow powder was identified as Compound (D-3-2) from the result of $^1$H-NMR spectrum (FIG. 1) and Field Desorption Mass Spectrum (FD-MS) measurement (yield: 90%). Further, the maximum absorption wavelength and the maximum fluorescent wavelength of the obtained Compound (D-3-2) among the toluene solvent were 484 nanometers and 533 nanometers respectively.

Example 1

A 130 nanometer-thick transparent electrode made of indium tin oxide was formed on a glass substrate having a size of 25 mm×75 mm×1.1 mm. The glass substrate with the transparent electrode was cleaned by irradiation of ultraviolet ray and ozone. The thus cleaned glass substrate with the transparent electrode was mounted to a vacuum vapor deposition apparatus.

First, N',N"-bis[4-(diphenylamino)phenyl]-N',N"-diphenylbiphenyl-4,4'-diamine was vapor-deposited to form a hole injecting layer having a thickness of 60 nanometers, and then N,N,N',N'-tetrakis(4-biphenyl)-4,4'-benzidine was vapor-deposited on the hole injecting layer to form a hole transporting layer having a thickness of 20 nanometers. Then, 10,10'-bis [1,1',4',1"]terphenyl-2-yl-9,9'-bianthracenyl and the foregoing Compound (D-1-5) as a doping material were simultaneously vapor-deposited at a weight ratio of 40:2 on the hole transporting layer to form a light emitting layer having a thickness of 40 nanometers.

Next, tris(8-quinolinolato)aluminum was vapor-deposited on the light emitting layer to form an electron injecting layer having a thickness of 20 nanometers. Subsequently, lithium fluoride was deposited up to 1 nanometer in thickness and then, aluminum was deposited up to 150 nanometers in thickness. The aluminum/lithium fluoride layer works as a cathode. An organic EL device was fabricated in the manner described above.

As a result of subjecting the organic EL device to a test by feeding electric current, it was confirmed that a blue light [CIE(0.14, 0.21)] with a luminance of 910 cd/m² (peak wavelength of light emission: 470 nanometers) and current efficiency of 9 cd/A was emitted at a voltage of 6.5 V and a current density of 10 mA/cm². Further, as a result of subjecting the device to a continuous test by feeding DC electric current starting at an initial luminance of 500 cd/m², it was confirmed that the half lifetime thereof was 20,000 hours or longer, which was within a sufficiently practical range.

Example 2

An organic EL device was fabricated in accordance with the same procedures as those conducted in Example 1 except that Compound (D-1-5) was replaced with Compound (D-3-1) as the doping material.

As a result of subjecting the organic EL device to a test by feeding electric current, it was confirmed that a green light with a luminance of 1400 cd/m² (peak wavelength of light emission: 540 nanometers) and current efficiency of 14 cd/A was emitted at a voltage of 6.5 V and a current density of 10 mA/cm². Further, as a result of subjecting the device to a continuous test by feeding DC electric current starting at an initial luminance of 1,000 cd/m², it was confirmed that the half lifetime thereof was 20,000 hours or longer, which was within a sufficiently practical range.

Example 3

An organic EL device was fabricated in accordance with the same procedures as those conducted in Example 1 except that Compound (D-1-5) was replaced with Compound (D-3-2) as the doping material together with simultaneously vapor-depositing at a weight ratio of 40:3 (host:dopant).

As a result of subjecting the organic EL device to a test by feeding electric current, it was confirmed that a green light with a luminance of 1600 cd/m² (peak wavelength of light emission: 545 nanometers) and current efficiency of 16 cd/A was emitted at a voltage of 6.5 V and a current density of 10 mA/cm². Further, as a result of subjecting the device to a continuous test by feeding DC electric current starting at an initial luminance of 1000 cd/m², it was confirmed that the half lifetime thereof was 20,000 hours or longer, which was within a sufficiently practical range.

Comparative Example 1

An organic EL device was fabricated in accordance with the same procedures as those conducted in Example 1 except that Compound (D-1-5) was replaced with 3,8-dimethyl-1,6-bis(3-methyldiphenylamino)pyrene compound as a doping material.

As a result of subjecting the organic EL device to a test by feeding electric current, it was confirmed that a blue light with a luminance of 805 cd/m² (peak wavelength of light emission: 465 nanometers) and current efficiency of 8 cd/A was emitted at a voltage of 6.5 V and a current density of 10 mA/cm², however, CIE chromaticity coordinate was (0.17, 0.25). Namely, the light emission spectrum was broadened in the long-wavelength direction because of a molecular association between compounds, thus, the color purity was deteriorated.

Comparative Example 2

An organic EL device was fabricated in accordance with the same procedures as those conducted in Example 3 except that Compound (D-3-2) was replaced with 9,10-diphenylamino-anthracene.

As a result of subjecting the organic EL device to a test by feeding electric current, it was confirmed that a green light with a luminance of 1030 cd/m² (peak wavelength of light emission: 514 nanometers) and current efficiency of 10.3 cd/A was emitted at a voltage of 6.5 V and a current density of 10 mA/cm². Further, as a result of subjecting the device to a continuous test by feeding DC electric current starting at an initial luminance of 1000 cd/m², it was confirmed that the half lifetime thereof was 10,000 hours. Namely, it is estimated that when the anthracene skeleton has no substituent, half lifetime shortens because of an association between compounds each other.

From the results of the above Examples and Comparative Examples, it was verified that bonding a silyl group with a fused polycyclic hydrocarbon group such as pyrene or anthracene prevents association between compounds and prolongs half lifetime of the EL device employing the aromatic amine derivative.

INDUSTRIAL APPLICABILITY

The organic EL device using the aromatic amine derivative according to the present invention exhibits excellent luminance, even under low applied voltage, and enhanced efficiency of light emission and further, the device is free from deterioration in properties even after being used for a long period of time and, therefore, has a prolonged lifetime. Resultantly, the EL device is useful as a flat panel light emitting member for a wall-hanging type television or as a light source of backlight and the like for display devices.

The invention claimed is:
1. An aromatic amine derivative represented by the following general formula (I):

wherein
X represents a substituted or unsubstituted fused polycyclic hydrocarbon group having 10 to 50 ring carbon atoms;
$A_1$ to $A_4$ each independently represents a substituted or unsubstituted aryl group having 5 to 50 ring carbon atoms, a substituted or unsubstituted alkyl group having 1 to 50 carbon atoms, wherein the alkyl group is selected from the group consisting of an ethyl group, a propyl group, an isopropyl group, a butyl group, a sec-butyl group, a tert-butyl group, a pentyl group, a hexyl group, a heptyl group, an octyl group, a stearyl group, a trichloromethyl group and a trifluoromethyl group, a substituted or unsubstituted cycloalkyl group having 3 to 50 ring carbon atoms, a substituted or unsubstituted aralkyl group having 6 to 50 ring carbon atoms or a substituted or unsubstituted heterocyclic group having 5 to 50 ring carbon atoms;

$R_1$ represents a substituted or unsubstituted silyl group having 3 to 20 carbon atoms, wherein the substituted silyl group is selected from the group consisting of a trimethylsilyl group, a triethylsilyl group, a t-butyldimethylsilyl group, a vinyldimethylsilyl group, a propyldimethylsilyl group, a triphenylsilyl group, a dimethylphenylsilyl group and a diethylmethylsilyl group;

$R_2$ is selected from the group consisting of: a hydrogen atom; a substituted or unsubstituted alkyl group having 1 to 50 carbon atoms, wherein the substituted alkyl group is selected from the group consisting of a methyl group, an ethyl group, a propyl group, an isopropyl group, a butyl group, a sec-butyl group, a tert-butyl group, a pentyl group, a hexyl group, a heptyl group, an octyl group, a stearyl group, a trichloromethyl group, and a trifluoromethyl group; a substituted or unsubstituted aryl group having 5 to 50 ring carbon atoms; a substituted or unsubstituted aralkyl group having 6 to 50 ring carbon atoms; a substituted or unsubstituted cycloalkyl group having 3 to 50 ring carbon atoms; a substituted or unsubstituted alkoxyl group having 1 to 50 carbon atoms; a substituted or unsubstituted aryloxy group having 5 to 50 ring carbon atoms; a substituted or unsubstituted arylamino group having 5 to 50 ring carbon atoms; a substituted or unsubstituted alkylamino group having 1 to 20 carbon atoms; and a substituted or unsubstituted heterocyclic group having 5 to 50 ring carbon atoms;

a represents an integer of 1 to 3, b represents an integer of 1 to 2, c represents an integer of 0 to 4, and when a, b or c is 2 or greater, a plural of $-NA_3A_4$ may be the same as or different from each other, a plural of $R_1$ may be the same as or different from each other, and a plural of $R_2$ may be the same as or different from each other, respectively.

2. The aromatic amine derivative according to claim 1, which is represented by the following general formula (II):

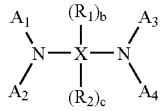

(II)

wherein X, $A_1$ to $A_4$, $R_1$, $R_2$, b and c are the same as defined in claim 1.

3. An aromatic amine derivative represented by the following general formula (III):

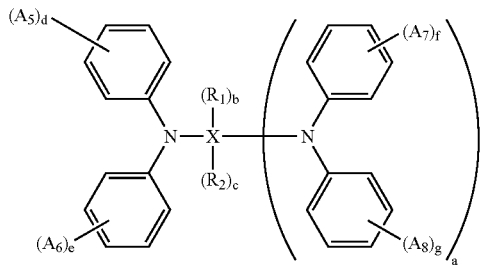

(III)

wherein

X represents a substituted or unsubstituted fused polycyclic hydrocarbon group having 10 to 50 ring carbon atoms;

$R_1$ represents a substituted or unsubstituted silyl group having 3 to 20 carbon atoms, wherein the substituted silyl group is selected from the group consisting of a trimethylsilyl group, a triethylsilyl group, a t-butyldimethylsilyl group, a vinyldimethylsilyl group, a propyldimethylsilyl group, a triphenylsilyl group, a dimethylphenylsilyl group and a diethylmethylsilyl group;

$R_2$ is selected from the group consisting of: a hydrogen atom; a substituted or unsubstituted alkyl group having 1 to 50 carbon atoms, wherein the substituted alkyl group is selected from the group consisting of a methyl group, an ethyl group, a propyl group, an isopropyl group, a butyl group, a sec-butyl group, a tert-butyl group, a pentyl group, a hexyl group, a heptyl group, an octyl group, a stearyl group, a trichloromethyl group, and a trifluoromethyl group; a substituted or unsubstituted aryl group having 5 to 50 ring carbon atoms; a substituted or unsubstituted aralkyl group having 6 to 50 ring carbon atoms; a substituted or unsubstituted cycloalkyl group having 3 to 50 ring carbon atoms; a substituted or unsubstituted alkoxyl group having 1 to 50 carbon atoms; a substituted or unsubstituted aryloxy group having 5 to 50 ring carbon atoms; a substituted or unsubstituted arylamino group having 5 to 50 ring carbon atoms; a substituted or unsubstituted alkylamino group having 1 to 20 carbon atoms; and a substituted or unsubstituted heterocyclic group having 5 to 50 ring carbon atoms;

a represents an integer of 1 to 3, b represents an integer of 1 to 2, c represents an integer of 0 to 4, and when a, b or c is 2 or greater, a plural of $-N(Ph(A_7)_f)(Ph(A_8)_g)$ may be the same as or different from each other, a plural of $R_1$ may be the same as or different from each other, and a plural of $R_2$ may be the same as or different from each other, respectively, $A_5$ to $A_8$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxyl group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted silyl group having 3 to 20 carbon atoms or a substituted or unsubstituted heterocyclic group having 5 to 50 ring carbon atoms;

d, e, f and g each independently represents an integer of 0 to 5, and when d, e, f and/or g is an integer of 2 or greater, a plural of $A_5$ to $A_8$ may be the same as or different from each other, and may bond to each other to form a saturated or unsaturated ring.

4. The aromatic amine derivative according to any one of claims 1 to 3, wherein X in the foregoing general formula (I), (II) or (III) represents a moiety of naphthalene, phenanthrene, fluoranthene, anthracene, pyrene, perylene, coronene, chrysene, picene, diphenylanthracene, fluorene, triphenylene, rubicene, benzanthracene, phenylanthracene, bisanthracene, dianthracenylbenzene or dibenzanthracene.

5. A doping material for an organic electroluminescence device comprising the aromatic amine derivative according to any one of claims 1 to 3.

6. An organic electroluminescence device which comprises one or more organic thin film layers comprising at least a light emitting layer sandwiched between a cathode and an anode, wherein at least one of the organic thin film layers comprises one or more of the aromatic amine derivatives according to any one of claims 1 to 3.

7. An organic electroluminescence device which comprises one or more organic thin film layers comprising at least a light emitting layer sandwiched between a cathode and an anode, wherein the light emitting layer of at least one of the organic thin film layers comprises one or more of the aromatic amine derivatives according to any one of claims 1 to 3.

8. An organic electroluminescence device which comprises one or more organic thin film layers comprising at least a light emitting layer sandwiched between a cathode and an anode, wherein the light emitting layer of at least one of the organic thin film layers comprises one or more of the aromatic amine derivatives according to any one of claims 1 to 3 in an amount of 0.1 to 20% by weight.

9. The aromatic amine derivative according to claim 1, wherein $A_1$ to $A_4$ each independently represents a substituted or unsubstituted aryl group having 5 to 50 ring carbon atoms, a substituted or unsubstituted alkyl group having 1 to 50 carbon atoms, wherein the alkyl group is selected from the group consisting of a propyl group, an isopropyl group, a butyl group, a sec-butyl group, a tert-butyl group, a pentyl group, a hexyl group, a heptyl group, an octyl group, a stearyl group, a trichloromethyl group and a trifluoromethyl group, a substituted or unsubstituted cycloalkyl group having 3 to 50 ring carbon atoms, a substituted or unsubstituted aralkyl group having 6 to 50 ring carbon atoms or a substituted or unsubstituted heterocyclic group having 5 to 50 ring carbon atoms.

10. The aromatic amine derivative according to claim 2, wherein $A_1$ to $A_4$ each independently represents a substituted or unsubstituted aryl group having 5 to 50 ring carbon atoms, a substituted or unsubstituted alkyl group having 1 to 50 carbon atoms, wherein the alkyl group is selected from the group consisting of a propyl group, an isopropyl group, a butyl group, a sec-butyl group, a tert-butyl group, a pentyl group, a hexyl group, a heptyl group, an octyl group, a stearyl group, a trichloromethyl group and a trifluoromethyl group, a substituted or unsubstituted cycloalkyl group having 3 to 50 ring carbon atoms, a substituted or unsubstituted aralkyl group having 6 to 50 ring carbon atoms or a substituted or unsubstituted heterocyclic group having 5 to 50 ring carbon atoms.

* * * * *